United States Patent
Asakawa et al.

(10) Patent No.: US 7,247,653 B2
(45) Date of Patent: Jul. 24, 2007

(54) PHARMACEUTICAL COMPOSITION

(75) Inventors: Naoki Asakawa, Takatsuki (JP); Masao Nagao, Kashiba (JP); Jun Sato, Kawanishi (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/198,710

(22) Filed: Aug. 5, 2005

(65) Prior Publication Data

US 2005/0272701 A1    Dec. 8, 2005

Related U.S. Application Data

(63) Continuation of application No. 10/343,287, filed as application No. PCT/JP01/06905 on Aug. 10, 2001, now Pat. No. 6,951,885.

(30) Foreign Application Priority Data

Aug. 10, 2000 (JP) .............................. 2000-247947
Aug. 10, 2000 (JP) .............................. 2000-247948

(51) Int. Cl.
  *A61K 31/24* (2006.01)
  *A61K 31/715* (2006.01)
(52) U.S. Cl. ......................................... 514/534; 514/58
(58) Field of Classification Search ..................... None
  See application file for complete search history.

(56) References Cited

U.S. PATENT DOCUMENTS

| | | | |
|---|---|---|---|
| 4,727,064 A | * | 2/1988 | Pitha ............................. 514/58 |
| 5,536,623 A | | 7/1996 | Ohmachi et al. |
| 6,495,604 B1 | | 12/2002 | Ichimori et al. |

FOREIGN PATENT DOCUMENTS

| | | |
|---|---|---|
| EP | 0 555 693 | 8/1993 |
| EP | 0 605 753 | 7/1994 |
| EP | 0 931 545 | 7/1999 |
| EP | 1 063 228 | 12/2000 |
| EP | 1 209 149 | 5/2002 |
| JP | 62026220 | 2/1987 |
| JP | 1221312 | 4/1989 |
| JP | 5139971 | 6/1993 |
| JP | 6157330 | 7/1994 |
| JP | 8301763 | 11/1996 |
| JP | 9048730 | 2/1997 |
| JP | 2000095682 | 4/2000 |
| JP | 2001261557 | 9/2001 |
| WO | WO 94/12031 | 6/1994 |
| WO | WO 96/38175 | 12/1996 |
| WO | WO 99/46242 | 9/1999 |
| WO | WO 01/56562 | 9/2001 |

OTHER PUBLICATIONS

The Merck Index, 11th ed. published by Merck & Co., Inc. (1989), cit. #2724, p. 425.

* cited by examiner

*Primary Examiner*—Raymond J. Henley, III
(74) *Attorney, Agent, or Firm*—Foley & Lardner LLP

(57) ABSTRACT

The present invention relates to a pharmaceutical composition containing a cycloalkene compound, a salt thereof or a prodrug thereof, and a nonionic surfactant and/or a cyclodextrin derivative readily soluble in water, and a method for improving solubility, stability or coloring property of the compound, a salt thereof or a prodrug thereof.

9 Claims, No Drawings

PHARMACEUTICAL COMPOSITION

This application is a continuation of U.S. patent application Ser. No. 10/343,287 filed Jan. 29, 2003, now U.S. Pat. No. 6,951,885, issued Oct. 4. 2005, which was the National Phase filing of International Patent Application No. PCT/JP01/06905, filed Aug. 10, 2001.

TECHNICAL FIELD

The present invention relates to a pharmaceutical composition wherein solubility or stability of a water-insoluble or slightly water-soluble cycloalkene compound is improved, and a method for improving solubility or stability of the cycloalkene compound.

BACKGROUND ART

WO 99/46242 describes that (i) a compound represented by the formula:

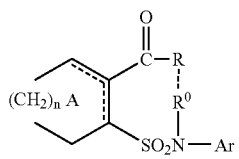

(Iaa)

wherein R represents an aliphatic hydrocarbon group optionally having substituents, an aromatic hydrocarbon group optionally having substituents, a heterocyclic group optionally having substituents, a group represented by the formula: —OR$^1$ (wherein R$^1$ represents a hydrogen atom or an aliphatic hydrocarbon group optionally having substituents) or a group represented by the formula:

(wherein R$^{1b}$ represents a hydrogen atom or an aliphatic hydrocarbon group optionally having substituents, R$^{1c}$ is, the same as or different from R$^{1b}$, a hydrogen atom or an aliphatic hydrocarbon group optionally having substituents, R$^0$ represents a hydrogen atom or an aliphatic hydrocarbon group, or R and R$^0$ represent a bond with each other, ring A is a cycloalkene substituted by 1 to 4 substituents selected from (1) an aliphatic hydrocarbon group optionally having substituents, (2) an aromatic hydrocarbon group optionally having substituents, (3) a group represented by the formula: —OR$^1$ (wherein R$^1$ is as defined above) and (4) a halogen atom, Ar represents an aromatic hydrocarbon group optionally having substituents, a group represented by the formula:

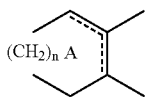

represents a group represented by the formula:

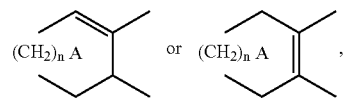

and n is an integer of 1 to 4, and (ii) a compound represented by the formula:

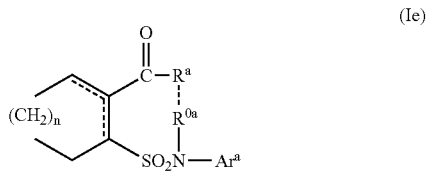

(Ie)

wherein R$^a$ represents an aliphatic hydrocarbon group optionally having substituents, an aromatic hydrocarbon group optionally having substituents, a heterocyclic group optionally having substituents, a group represented by the formula: —OR$^{1a}$ (wherein R$^{1a}$ represents a hydrogen atom or an aliphatic hydrocarbon group optionally having substituents) or a group represented by the formula:

(wherein R$^{1a}$ is as defined above, R$^{1b}$ is, the same as or different from R$^{1a}$, a hydrogen atom or an aliphatic hydrocarbon group optionally having substituents, R$^{0a}$ represents a hydrogen atom or an aliphatic hydrocarbon group, or R$^a$ and R$^{0a}$ represent a bond with each other, Ar$^a$ represents an aromatic hydrocarbon group optionally having substituents, a group represented by the formula:

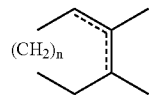

represents a group represented by the formula:

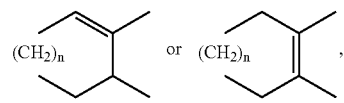

and n represents an integer of 1 to 4, a salt thereof and a prodrug thereof have a nitric oxide (NO) production-inhibiting effect and an inhibitory effect on the production of inflammatory cytokines, such as TNF-α, IL-1, IL-6 and the like, and are useful as a prophylactic and therapeutic agent against the diseases including cardiac diseases, autoimmune diseases, inflammatory diseases, central nervous system diseases, infectious diseases, sepsis, septic shock and the like.

DISCLOSURE OF THE INVENTION

The present invention aims at providing a pharmaceutical composition, wherein solubility, stability and the like of the above-mentioned compound are improved, and a method for improving solubility, stability and the like of the above-mentioned compound.

In view of the above-mentioned problems, the present inventors have conducted intensive studies and unexpectedly succeeded in obtaining a pharmaceutical composition, wherein solubility, stability, coloring property and the like of said compound are markedly improved, by mixing the above-mentioned compound, and a nonionic surfactant such as polyoxyethylene castor oil, polyoxyethylene hydrogenated castor oil and the like and/or a cyclodextrin derivative readily soluble in water. Based on this finding, the present inventors have further investigated and completed the present invention.

Accordingly, the present invention provides

[1] a pharmaceutical composition comprising (a) a compound represented by the formula (I):

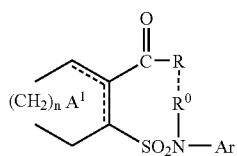

wherein R is an aliphatic hydrocarbon group optionally having substituents, an aromatic hydrocarbon group optionally having substituents, a heterocyclic group optionally having substituents, a group represented by the formula: —$OR^1$ (wherein $R^1$ is a hydrogen atom or an aliphatic hydrocarbon group optionally having substituents) or a group represented by the formula:

$$N\begin{array}{c}R^{1b}\\R^{1c}\end{array}$$

wherein $R^{1b}$ is a hydrogen atom or an aliphatic hydrocarbon group optionally having substituents, $R^{1c}$ is the same as or different from $R^{1b}$ and is a hydrogen atom or an aliphatic hydrocarbon group optionally having substituents, $R^0$ is a hydrogen atom or an aliphatic hydrocarbon group, or R and $R^0$ in combination represent a bond, ring $A^1$ is a cycloalkene optionally substituted by 1 to 4 substituents selected from (1) an aliphatic hydrocarbon group optionally having substituents, (2) an aromatic hydrocarbon group optionally having substituents, (3) a group represented by the formula: —$OR^1$ (wherein $R^1$ is as defined above) and (4) a halogen atom, Ar is an aromatic hydrocarbon group optionally having substituents, a group represented by the formula:

represents a group represented by the formula:

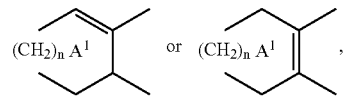

and n is an integer of 1 to 4, a salt thereof or a prodrug thereof, and (b) a nonionic surfactant and/or a cyclodextrin derivative readily soluble in water,

[2] a pharmaceutical composition comprising a compound represented by the formula (I):

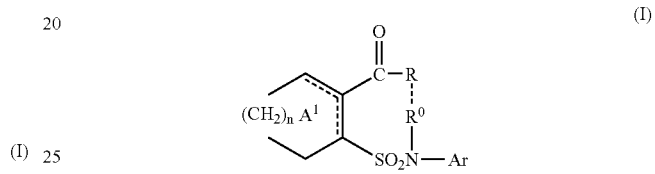

wherein each symbol is as defined in [1], a salt thereof or a prodrug thereof, and a nonionic surfactant,

[3] the composition of [2], wherein the nonionic surfactant is polyoxyethylene castor oil or polyoxyethylene hydrogenated castor oil,

[4] the composition of [2], further comprising ethanol,

[5] the composition of [2], wherein the compound is (A) d-ethyl 6-[N-(2-chloro-4-fluorophenyl)sulfamoyl]-1-cyclohexene-1-carboxylate, (B) d-ethyl 6-[N-(2,4-difluorophenyl)sulfamoyl]-1-cyclohexene-1-carboxylate, (C) ethyl 6-[N-(2-chlorophenyl)sulfamoyl]-1-cyclohexene-1-carboxylate, (D) ethyl 6-[N-(2-chloro-4-methylphenyl)sulfamoyl]-1-cyclohexene-1-carboxylate, or a salt thereof,

[6] the composition of [2], wherein a content of the nonionic surfactant is about 10 wt %-about 70 wt % of the whole composition,

[7] the composition of [4], wherein a content of the ethanol is about 30 wt %-about 90 wt % of the whole composition,

[8] the composition of [4], wherein a mixing ratio of the nonionic surfactant and ethanol is about 90 parts by weight-about 10 parts by weight of ethanol relative to about 10 parts by weight-about 90 parts by weight of the nonionic surfactant,

[9] the composition of [2], which is used as an injectable composition,

[10] the composition of [9], which is a non-emulsified composition,

[11] the composition of [2], which is clear

[12] the composition of [2], which is a nitric oxide and/or a cytokine production inhibitor,

[13] the composition of [2], which is an agent for the prophylaxis or treatment of a cardiac disease, an autoimmune disease or septic shock,

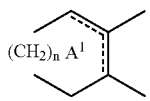

[14] a method for improving solubility, stability or coloring property of a compound represented by the formula (I):

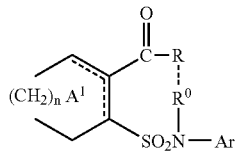

wherein each symbol is as defined in [1], a salt thereof or a prodrug thereof, which comprises mixing said compound, a salt thereof or a prodrug thereof, with a nonionic surfactant,

[15] a method for the prophylaxis or treatment of a cardiac disease, an autoimmune disease or septic shock, which comprises administrating an effective amount of the composition of [2] to a mammal,

[16] use of the composition of [2] for manufacturing an agent for the prophylaxis or treatment of a cardiac disease, an autoimmune disease or septic shock,

[17] a pharmaceutical composition comprising a compound represented by the formula (I):

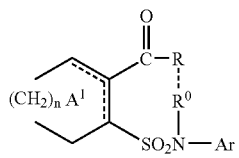

wherein each symbol is as defined in [1], a salt thereof or a prodrug thereof, and a cyclodextrin derivative readily soluble in water,

[18] the composition of [17], wherein the cyclodextrin derivative readily soluble in water is represented by the formula:

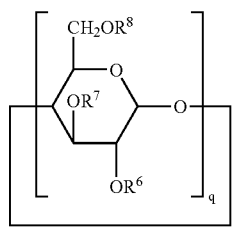

wherein q is an integer of 6 to 12, $R^6$, $R^7$ and $R^8$ are the same or different in individual repeating unit and each is a hydrogen atom, a dihydroxyalkyl group, a saccharide residue or a hydroxyalkyl group, and at least one of $R^6$, $R^7$ and $R^8$ is a dihydroxyalkyl group, a saccharide residue or a hydroxyalkyl group,

[19] the composition of [18], wherein at least one of $R^6$, $R^7$ and $R^8$ is a saccharide residue, and the remaining groups are hydrogen atoms,

[20] the composition of [18] or [19], wherein the saccharide residue is selected from the group consisting of glucosyl group, maltosyl group, maltotriosyl group and dimaltosyl group,

[21] the composition of [17], wherein the cyclodextrin derivative readily soluble in water is maltosyl-β-cyclodextrin,

[22] the composition of [17], which comprises about 0.1-about 100 mol of the cyclodextrin derivative readily soluble in water per 1 mol of the compound represented by the formula (I), a salt thereof or a prodrug thereof,

[23] the composition of [17], which comprises about 1-about 5 mol of the cyclodextrin derivative readily soluble in water per 1 mol of the compound represented by the formula (I), a salt thereof or a prodrug thereof,

[24] the composition of [17], wherein said compound is (A) d-ethyl 6-[N-(2-chloro-4-fluorophenyl)sulfamoyl]-1-cyclohexene-1-carboxylate, (B) d-ethyl 6-[N-(2,4-difluorophenyl)sulfamoyl]-1-cyclohexene-1-carboxylate, (C) ethyl 6-[N-(2-chlorophenyl)sulfamoyl]-1-cyclohexene-1-carboxylate, (D) ethyl 6-[N-(2-chloro-4-methylphenyl)sulfamoyl]-1-cyclohexene-1-carboxylate, or a salt thereof,

[25] the composition of [17], which is used as an injectable composition,

[26] the composition of [17], which is a nitric oxide and/or a cytokine production inhibitor,

[27] the composition of [17], which is an agent for the prophylaxis or treatment of a cardiac disease, an autoimmune disease or septic shock,

[28] a method for improving solubility, stability or coloring property of a compound represented by the formula (I):

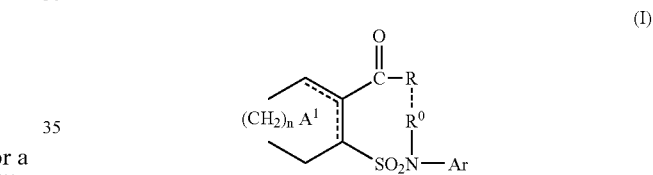

wherein each symbol is as defined in [1], a salt thereof or a prodrug thereof, which comprises mixing said compound, a salt thereof or a prodrug thereof with a cyclodextrin derivative readily soluble in water,

[29] a method for the prophylaxis or treatment of a cardiac disease, an autoimmune disease or septic shock, which comprises administrating an effective amount of the composition of [17] to a mammal, and

[30] use of the composition of [17] for manufacturing an agent for the prophylaxis or treatment of a cardiac disease, an autoimmune disease or septic shock.

The present invention also provides

[31] the composition of [1], [2] or [17], wherein the compound represented by the formula (I) is (i) a compound represented by the formula:

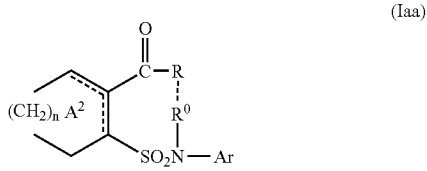

wherein R is an aliphatic hydrocarbon group optionally having substituents, an aromatic hydrocarbon group optionally having substituents, a heterocyclic group optionally having substituents, a group represented by the formula: —OR$^1$ (wherein R$^1$ is a hydrogen atom or an aliphatic hydrocarbon group optionally having substituents) or a group represented by the formula:

wherein R$^{1b}$ is a hydrogen atom or an aliphatic hydrocarbon group optionally having substituents, R$^{1c}$ is the same as or different from R$^{1b}$ and is a hydrogen atom or an aliphatic hydrocarbon group optionally having substituents, R$^0$ is a hydrogen atom or an aliphatic hydrocarbon group, or R and R$^0$ in combination represent a bond, ring A$^2$ is a cycloalkene substituted by 1 to 4 substituents selected from (1) an aliphatic hydrocarbon group optionally having substituents, (2) an aromatic hydrocarbon group optionally having substituents, (3) a group represented by the formula: —OR$^1$ (wherein R$^1$ is as defined above) and (4) a halogen atom, Ar is an aromatic hydrocarbon group optionally having substituents, a group represented by the formula:

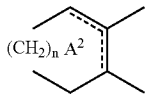

represents a group represented by the formula:

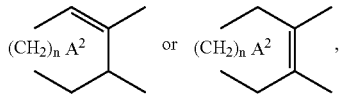

and n is an integer of 1 to 4, or
(ii) a compound represented by the formula:

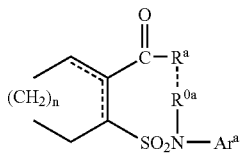
(Ie)

wherein R$^a$ is an aliphatic hydrocarbon group optionally having substituents, an aromatic hydrocarbon group optionally having substituents, a heterocyclic group optionally having substituents, a group represented by the formula: —OR$^{1a}$ (wherein R$^{1a}$ is a hydrogen atom or an aliphatic hydrocarbon group optionally having substituents) or a group represented by the formula:

wherein R$^{1a}$ is as defined above, and R$^{1b}$ is the same as or different from R$^{1a}$ and is a hydrogen atom or an aliphatic hydrocarbon group optionally having substituents, R$^{0a}$ is a hydrogen atom or an aliphatic hydrocarbon group, or R$^a$ and R$^{0a}$ in combination represent a bond, Ar$^a$ is an aromatic hydrocarbon group optionally having substituents, a group represented by the formula:

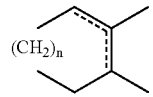

represents a group represented by the formula:

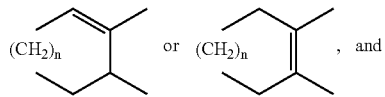

n is an integer of 1 to 4,

[32] the composition of [31], wherein the compound represented by the formula (Iaa) is a compound represented by the formula:

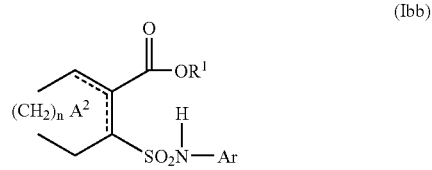
(Ibb)

wherein each symbol is as defined in [1],

[33] the composition of [31], wherein the ring A$^2$ is a cycloalkene substituted by a lower alkyl, a phenyl or a halogen, R$^1$ is a lower alkyl group, Ar is a phenyl group optionally having substituents, and n is 2,

[34] the composition of [31], wherein the compound represented by the formula (Ie) is a compound of the formula:

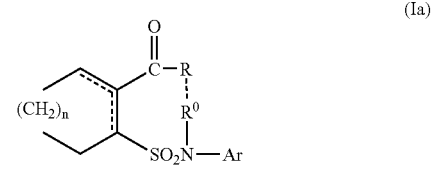
(Ia)

wherein R is an aliphatic hydrocarbon group optionally having substituents, an aromatic hydrocarbon group optionally having substituents, a heterocyclic group optionally having substituents, a group represented by the formula: —OR$^1$ (wherein R$^1$ is a hydrogen atom or an aliphatic hydrocarbon group optionally having substituents) or a group represented by the formula:

(wherein $R^{1b}$ is a hydrogen atom or an aliphatic hydrocarbon group optionally having substituents, and $R^{1c}$ is the same as or different from $R^{1b}$ and is a hydrogen atom or an aliphatic hydrocarbon group optionally having substituents), $R^0$ is a hydrogen atom or an aliphatic hydrocarbon group, or R and $R^0$ in combination represent a bond, Ar is an aromatic hydrocarbon group optionally having substituents, a group represented by the formula:

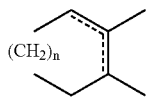

represents a group represented by the formula:

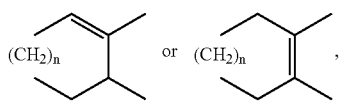

and n is an integer of 1 to 4, provided that when n is 1 or 2 and (i) $R^1$ is a hydrogen atom or an ethyl group, $R^0$ is a methyl group and Ar is a phenyl group or (ii) R and $R^0$ in combination represent a bond and Ar is a phenyl group, a 2-methylphenyl group, a 4-bromophenyl group, a 4-methoxyphenyl group or a 2,6-dimethylphenyl group, a group represented by the formula:

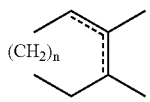

should be a group represented by the formula:

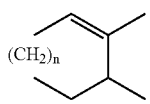

[35] the composition of [34], wherein the compound represented by the formula (Ia) is a compound represented by the formula:

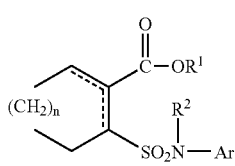

(Ib)

wherein $R^2$ is a hydrogen atom or an aliphatic hydrocarbon group, and $R^1$, Ar, n and the group represented by the formula:

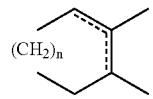

are as defined in [33], provided that when n is 1 or 2, Ar is a phenyl group, $R^1$ is a hydrogen atom or an ethyl group and $R^2$ is a methyl group, the group represented by the formula:

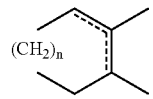

should be a group represented by the formula:

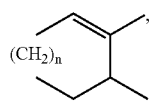

[36] the composition of [35], wherein $R^1$ is a lower alkyl group optionally having substituents,
[37] the composition of [35], wherein $R^1$ is an ethyl group,
[38] the composition of [35], wherein $R^2$ is a hydrogen atom or a lower alkyl group,
[39] the composition of [35], wherein $R^2$ is a hydrogen atom,
[40] the composition of [35], wherein Ar is a phenyl group optionally having substituents,
[41] the composition of [35], wherein Ar is a phenyl group substituted by a halogen and/or a lower alkyl,
[42] the composition of [35], wherein Ar is a group represented by the formula:

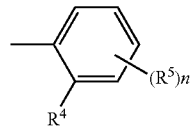

wherein $R^4$ and $R^5$ are the same or different and each is a halogen atom or a lower alkyl group, and n is an integer of 0 to 2,
[43] the composition of [35], wherein the halogen atom is a fluorine atom or a chlorine atom,
[44] the composition of [35], wherein the group represented by the formula:

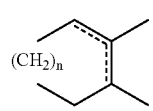

is a group represented by the formula:

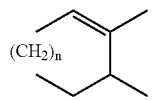

wherein n is as defined in [34],

[45] the composition of [35], wherein n is 1 to 3,

[46] the composition of [35], wherein $R^1$ is a lower alkyl group optionally having substituents, $R^2$ is a hydrogen atom or a lower alkyl group, Ar is a phenyl group optionally having substituents, and n is 1, 2 or 3,

[47] the composition of [35], wherein $R^1$ is a lower alkyl group optionally having substituents, $R^2$ is a hydrogen atom, Ar is a phenyl group substituted by a halogen atom, and n is 2,

[48] the composition of [34], wherein the compound represented by the formula (Ia) is a compound represented by the formula:

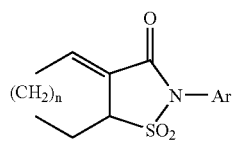
(Ic)

wherein Ar and n are as defined in [34],

[49] the composition of [48], wherein Ar is a phenyl group optionally having substituents, and n is 2,

[50] the composition of [34], wherein the compound represented by the formula (Ia) is a compound represented by the formula:

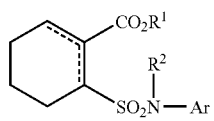
(Id)

wherein $R^1$, $R^2$ and Ar are as defined in [35], and the group represented by the formula:

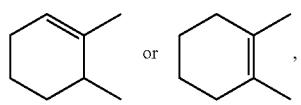

represents a group represented by the formula:

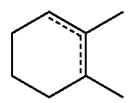 or 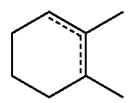, provided that when Ar is a phenyl group, $R^1$ is a hydrogen atom or an ethyl group and $R^2$ is a methyl group, the group represented by the formula:

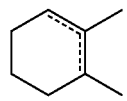

should be a group represented by the formula:

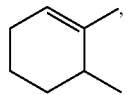,

[51] the composition of [31], wherein the compound represented by the formula (Ie) is a compound represented by the formula:

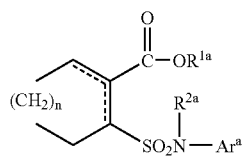
(If)

wherein $R^{2a}$ is a hydrogen atom or an aliphatic hydrocarbon group, and $R^{1a}$, $Ar^a$, n and the group represented by the formula:

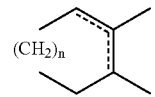

are as defined in [31], and

[52] the composition of [31], wherein the compound represented by the formula (Ie) is a compound represented by the formula:

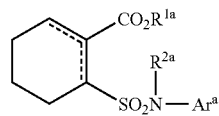
(Ig)

wherein $R^{1a}$, $R^{2a}$ and $Ar^a$ are as defined in [51] and the group represented by the formula:

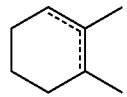

is a group represented by the formula:

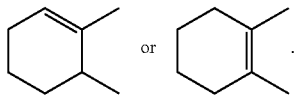

In the specification, R represents an aliphatic hydrocarbon group optionally having substituents, an aromatic hydrocarbon group optionally having substituents, a heterocyclic group optionally having substituents, a group represented by the formula: —OR$^1$ (wherein R$^1$ represents a hydrogen atom or an aliphatic hydrocarbon group optionally having substituents) or a group represented by the formula:

wherein R$^{1b}$ represents a hydrogen atom or an aliphatic hydrocarbon group optionally having substituents, R$^{1c}$ is the same as or different from R$^{1b}$ and is a hydrogen atom or an aliphatic hydrocarbon group optionally having substituents, or R forms a bond with R$^0$, with preference given to the group represented by the formula: —OR$^1$ (wherein R$^1$ is as defined above).

R$^a$ represents an aliphatic hydrocarbon group optionally having substituents, an aromatic hydrocarbon group optionally having substituents, a heterocyclic group optionally having substituents, a group represented by the formula: —OR$^{1a}$ (wherein R$^{1a}$ represents a hydrogen atom or an aliphatic hydrocarbon group optionally having substituents) or a group represented by the formula:

(wherein R$^{1a}$ is as defined above, R$^{1b}$ is the same as or different from R$^{1a}$ and is a hydrogen atom or an aliphatic hydrocarbon group optionally having substituents), or form a bond with R$^{0a}$, with preference given to the group represented by the formula: —OR$^{1a}$ (wherein R$^{1a}$ is as defined above).

When R and R$^0$ in combination represent a bond, the compound represented by the formula (Iaa) can be represented by the formula:

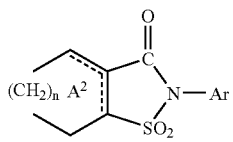

(Ihh)

wherein each symbol is as defined above, and specifically can be represented by the formula:

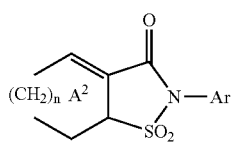

(Icc)

wherein each symbol is as defined above, or

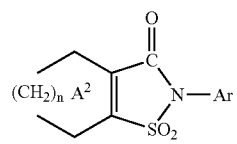

(Iii)

wherein each symbol is as defined above.

When R and R$^0$ in combination represent a bond, the compound represented by the formula (Ia) can be represented by the formula:

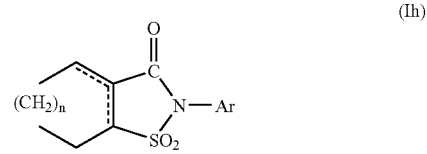

(Ih)

wherein each symbol is as defined above, and specifically can be represented by the formula:

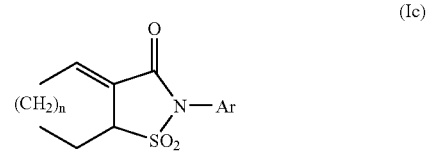

(Ic)

wherein each symbol is as defined above, or the formula:

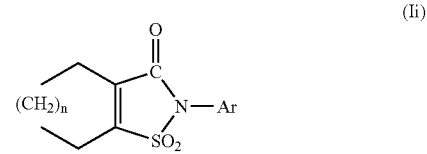

(Ii)

wherein each symbol is as defined above.

When R$^a$ and R$^{0a}$ in combination represent a bond, the compound represented by the formula (Ie) can be represented by the formula:

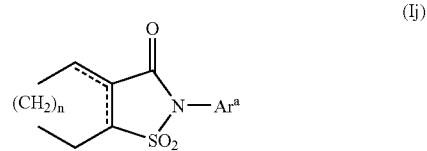

(Ij)

wherein each symbol is as defined above, and specifically can be represented by the formula:

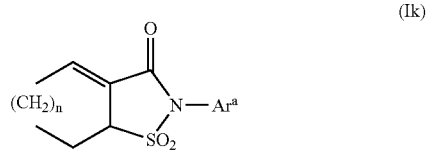

(Ik)

wherein each symbol is as defined above, or the formula:

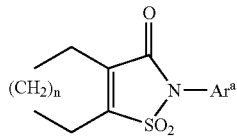
(Im)

wherein each symbol is as defined above.

When R is a group represented by the formula: —OR$^1$ (wherein R$^1$ is as defined above), the compound represented by the formula (Iaa) can be represented by the formula:

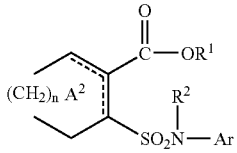
(Ibb)

wherein each symbol is as defined above, and specifically can be represented by the formula:

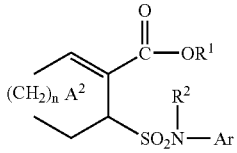
(Inn)

wherein each symbol is as defined above, or the formula:

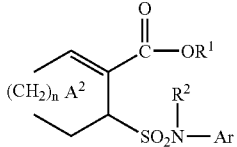
(Ioo)

wherein each symbol is as defined above.

When R is a group represented by the formula: —OR$^1$ (wherein R$^1$ is as defined above), the compound represented by the formula (Ia) can be represented by the formula:

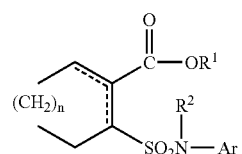
(Ib)

wherein each symbol is as defined above, and specifically can be represented by the formula:

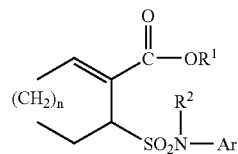
(In)

wherein each symbol is as defined above, or the formula:

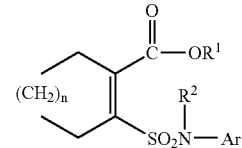
(Io)

wherein each symbol is as defined above.

When R$^a$ is a group represented by the formula: —OR$^{1a}$ (wherein R$^{1a}$ is as defined above), the compound represented by the formula (Ie) can be represented by the formula:

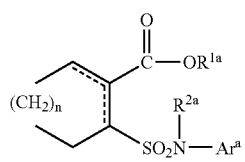
(If)

wherein each symbol is as defined above, and specifically can be represented by the formula:

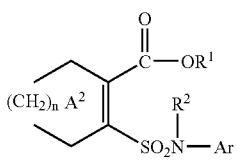
(Ip)

wherein each symbol is as defined above, or the formula:

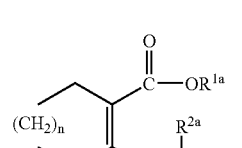
(Iq)

wherein each symbol is as defined above.

As the compound represented by the formula (Iaa), a compound represented by the formula (Icc) or the formula (Inn) is preferable, as the compound represented by the formula (Ia), a compound represented by the formula (Ic) or the formula (In) is preferable, and as the compound represented by the formula (Ie), a compound represented by the formula (Ik) or the formula (Ip) is preferable.

Similarly, the compound represented by the formula (Id) can be represented by the formula:

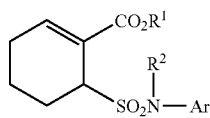
(Ir)

wherein each symbol is as defined above, or the formula:

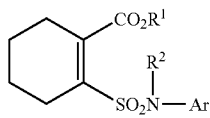
(Is)

wherein each symbol is as defined above, and the compound represented by the formula (Ig) can be represented by the formula:

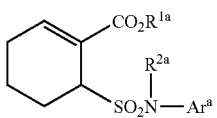
(It)

wherein each symbol is as defined above, or the formula:

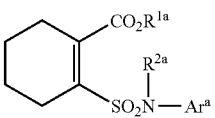
(Iu)

wherein each symbol is as defined above.

As the compound represented by the formula (Id), a compound represented by the formula (Ir) is preferable, and as the compound represented by the formula (Ig), a compound represented by the formula (It) is preferable.

In the compound represented by the formula (Ia), when n is 1 or 2, and (i) $R^1$ is a hydrogen atom or an ethyl group, $R^0$ is a methyl group and Ar is a phenyl group, or (ii) R and $R^0$ in combination represent a bond and Ar is a phenyl group, a 2-methylphenyl group, a 4-bromophenyl group, a 4-methoxyphenyl group or a 2,6-dimethylphenyl group, a group represented by the formula:

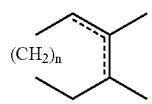

should be a group represented by the formula:

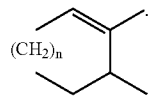

Furthermore, when n is 1 to 4, and (i) $R^1$ is a hydrogen atom or a lower alkyl group optionally having substituents, $R^0$ is a lower alkyl group optionally having substituents, and Ar is a phenyl group optionally having substituents, or (ii) R and $R^0$ in combination represent a bond and Ar is a phenyl group optionally having substituents, a group represented by the formula:

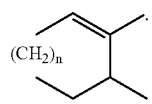

may be a group represented by the formula:

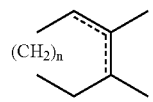

In the compound represented by the formula (Ib), when n is 1 or 2, $R^1$ is a hydrogen atom or an ethyl group, $R^0$ is a methyl group, and Ar is a phenyl group, a group represented by the formula:

should be a group represented by the formula:

Furthermore, when n is 1 to 4, and $R^1$ is a hydrogen atom or a lower alkyl group optionally having substituents, $R^0$ is a lower alkyl group optionally having substituents, and Ar is a phenyl group optionally having substituents, a group represented by the formula:

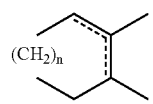

may be a group represented by the formula:

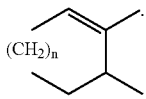

As the "aliphatic hydrocarbon group" of the "aliphatic hydrocarbon group optionally having substituents" represented by R, $R^1$, $R^{1a}$, $R^{1b}$ and $R^{1c}$, and the "aliphatic hydrocarbon group" represented by $R^0$, $R^{0a}$, $R^2$ and $R^{2a}$, for example, an alkyl group, a cycloalkyl group, a cycloalkylalkyl group, an alkenyl group, an alkynyl group, etc. are preferable.

As the alkyl group, for example, a linear or branched alkyl group having 1 to 20 carbon atoms (e.g., a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, a dodecyl group, etc.), and the like are preferable, and particularly, for example, a lower alkyl group having 1 to 6 carbon atoms (e.g., a methyl group, an ethyl group, an n-propyl group, an isopropyl group, an n-butyl group, an isobutyl group, a sec-butyl group, a tert-butyl group, etc.), and the like are preferable.

As the cycloalkyl group, for example, a cycloalkyl group having 3 to 10 carbon atoms (e.g., a cyclopropyl group, a cyclobutyl group, a cyclopentyl group, a cyclohexyl group, a cycloheptyl group, a cyclooctyl group, etc.), and the like are preferable, and particularly, for example, a cycloalkyl group having 3 to 6 carbon atoms (e.g., a cyclopropyl group, a cyclobutyl group, a cyclopentyl group, a cyclohexyl group, etc.), and the like are preferable.

As the cycloalkylalkyl group, for example, a cycloalkylalkyl group having 4 to 12 carbon atoms (e.g., a cyclopropylmethyl group, a cyclopentylmethyl group, a cyclohexylmethyl group, a cycloheptylmethyl group, etc.), and the like are preferable, and particularly, for example, a cycloalkylalkyl group having 4 to 8 (particularly 4 to 7) carbon atoms (e.g., a cyclopropylmethyl group, a cyclopentylmethyl group, a cyclohexylmethyl group, etc.), and the like are preferable.

As the alkenyl group, for example, a lower alkenyl group having 3 to 6 carbon atoms (e.g., a propenyl group, a butenyl group, a pentenyl group, etc.) are preferable, and particularly, for example, a lower alkenyl group having 3 or 4 carbon atoms (e.g., a propenyl group, a butenyl group, etc.), and the like are preferable.

As the alkynyl group, for example, a lower alkynyl group having 3 to 6 carbon atoms (e.g., a propynyl group, a butynyl group, a pentynyl group, etc.) are preferable, and particularly, for example, a lower alkynyl group having 3 or 4 carbon atoms (e.g., a propynyl group, a butynyl group, etc.), and the like are preferable.

As the "substituents" of the above-mentioned "aliphatic hydrocarbon group optionally having substituents", for example, a heterocyclic group, an oxo group, a hydroxy group, a $C_{1-6}$ alkoxy group, a $C_{3-10}$ (particularly $C_{3-6}$) cycloalkyloxy group, a $C_{6-10}$ aryloxy group, a $C_{7-19}$ (particularly $C_{7-12}$) aralkyloxy group, a heterocyclic oxy group, a $C_{1-6}$ alkylthio group (sulfur atom may be oxidized), a $C_{3-10}$ (particularly $C_{3-6}$) cycloalkylthio group (sulfur atom may be oxidized), a $C_{6-10}$ arylthio group (sulfur atom may be oxidized), a $C_{7-19}$ (particularly $C_{7-12}$) aralkylthio group (sulfur atom may be oxidized), a heterocyclic thio group, a heterocyclic sulfinyl group, a heterocyclic sulfonyl group, a nitro group, a halogen atom, a cyano group, a carboxyl group, a $C_{1-10}$ (particularly $C_{1-6}$) alkoxy-carbonyl group, a $C_{3-6}$ cycloalkyloxy-carbonyl group, a $C_{6-10}$ aryloxy-carbonyl group, a $C_{7-19}$ (particularly $C_{7-12}$) aralkyloxy-carbonyl group, a heterocyclic oxycarbonyl group, a $C_{6-10}$ aryl-carbonyl group, $C_{1-6}$ alkanoyl group, $C_{3-5}$ alkenoyl group, a $C_{6-10}$ aryl-carbonyloxy group, a $C_{2-6}$ alkanoyloxy group, a $C_{3-5}$ alkenoyloxy group, a carbamoyl group optionally having substituents, a thiocarbamoyl group optionally having substituents, a carbamoyloxy group optionally having substituents, a $C_{1-6}$ alkanoylamino group, a $C_{6-10}$ aryl-carbonylamino group, a $C_{1-10}$ (particularly $C_{1-6}$) alkoxy-carboxamido group, a $C_{6-10}$ aryloxy-carboxamido group, a $C_{7-19}$ (particularly $C_{7-12}$) aralkyloxy-carboxamido group, a $C_{1-10}$ (particularly $C_{1-6}$) alkoxy-carbonyloxy group, a $C_{6-10}$ aryloxy-carbonyloxy group, a $C_{7-19}$ (particularly $C_{7-12}$) aralkyloxy-carbonyloxy group, a $C_{3-10}$ (particularly $C_{3-6}$)cycloalkyloxy-carbonyloxy group, a ureido group optionally having substituents, a $C_{6-10}$ aryl group optionally having substituents, etc. are used.

These substituents are substituted at substitutable positions in the above-mentioned "aliphatic hydrocarbon group", wherein the substituents are not limited a single substituent but may be the same or different plural (2 to 4) substituents.

As the "$C_{1-6}$ alkoxy group", for example, a methoxy group, an ethoxy group, an n-propoxy group, an isopropoxy group, an n-butoxy group, a tert-butoxy group, an n-pentyloxy group, an n-hexyloxy group, etc. are used, as the "$C_{3-10}$ cycloalkyloxy group", for example, a cyclopropyloxy group, a cyclohexyloxy group, etc. are used, as the "$C_{6-10}$ aryloxy group", for example, a phenoxy group, a naphthyloxy group, etc. are used, as the "$C_{7-19}$ aralkyloxy group", for example, a benzyloxy group, a 1-phenylethyloxy group, a 2-phenylethyloxy group, a benzhydryloxy group, a 1-naphthylmethyloxy group, etc. are used, as the "$C_{1-6}$ alkylthio group (sulfur atom may be oxidized)", for example, a methylthio group, an ethylthio group, an n-propylthio group, an n-butylthio group, a methylsulfinyl group, a methylsulfonyl group, etc. are used, as the "$C_{3-10}$ cycloalkylthio group (sulfur atom may be oxidized)", for example, a cyclopropylthio group, a cyclohexylthio group, a cyclopentylsulfinyl group, a cyclohexylsulfonyl group, etc. are used, as the "$C_{6-10}$ arylthio group (sulfur atom may be oxidized)", for example, a phenylthio group, a naphthylthio group, a phenylsulfinyl group, a phenylsulfonyl group, etc. are used, as the "$C_{7-19}$ aralkylthio group (sulfur atom may be oxidized)", for example, a benzylthio group, a phenylethylthio group, a benzhydrylthio group, a benzylsulfinyl group, a benzylsulfonyl group, etc. are used, as the "halogen atom", for example, a fluorine atom, a chlorine atom, a bromine atom, an iodine atom, etc. are used, as the "$C_{1-10}$ alkoxy-carbonyl group", for example, a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, etc. are used, as the "$C_{3-6}$ cycloalkyloxycarbonyl group", for example, a cyclopropyloxycarbonyl group, a cyclopentyloxycarbonyl group, a cyclohexyloxycarbonyl group, a norbornyloxycarbonyl group, etc. are used, as the "$C_{6-10}$ aryloxy-carbonyl group", for example, a phenoxycarbonyl group, a naphthyloxycarbonyl group, etc. are used, as the "$C_{7-19}$ aralkyloxy-carbonyl group", for example, a benzyloxycarbonyl group, a benzhydryloxycarbonyl group, a 2-phenethyloxycarbonyl group, etc. are used, as the "$C_{6-10}$ aryl-carbonyl group", for example, a benzoyl group, a naphthoyl group, a phenylacetyl group, etc. are used, as the "$C_{1-6}$ alkanoyl group", for example, a formyl group, an acetyl group, a propionyl group, a butyryl group, a valeryl group, a pivaloyl group, etc. are used, as the "$C_{3-5}$ alkenoyl group", for example, an acryloyl group, a crotonoyl group, etc. are used, as the "$C_{6-10}$ aryl-carbonyloxy group", for example, a benzoyloxy group, a naphthoyloxy group, a phenylacetoxy group, etc. are used, as the "$C_{2-6}$ alkanoyloxy group", for example, an acetoxy group, a propionyloxy group, a butyryloxy group, a valeryloxy group, a pivaloyloxy group, etc. are used, and as the "$C_{3-5}$ alkenoyloxy group", for example, an acryloyloxy group, a crotonoyloxy group, etc. are used.

As the "carbamoyl group optionally having substituents", for example, a carbamoyl group or a cyclic aminocarbonyl group, which may be substituted by 1 or 2 substituents selected from $C_{1-4}$ alkyl (e.g., methyl, ethyl, etc.), a phenyl, a $C_{1-7}$ acyl (e.g., acetyl, propionyl, benzoyl, etc.), a $C_{1-4}$ alkoxy-phenyl (e.g., methoxyphenyl, etc.), etc. are used, and specifically, for example, a carbamoyl group, an N-methylcarbamoyl group, an N-ethylcarbamoyl group, an N,N-dimethylcarbamoyl group, an N,N-diethylcarbamoyl group, an N-phenylcarbamoyl group, an N-acetylcarbamoyl group, an N-benzoylcarbamoyl group, an N-(p-methoxyphenyl) carbamoyl group, a 1-pyrrolidinylcarbonyl group, a piperidinocarbonyl group, a 1-piperazinylcarbonyl group, a morpholinocarbonyl group, etc. are used. As the "thiocarbamoyl group optionally having substituents", for example, a thiocarbamoyl group which may be substituted by 1 or 2 substituents selected from $C_{1-4}$ alkyl (e.g., methyl, ethyl, etc.), phenyl, etc. are used, and specifically, for example, a thiocarbamoyl group, an N-methylthiocarbamoyl group, an N-phenylthiocarbamoyl group, etc. are used. As the "carbamoyloxy group optionally having substituents", for example, a carbamoyloxy group which may be substituted by 1 or 2 substituents selected from $C_{1-4}$ alkyl (e.g., methyl, ethyl, etc.), phenyl, etc. are used, and specifically, for example, a carbamoyloxy group, an N-methylcarbamoyloxy group, an N,N-dimethylcarbamoyloxy group, an N-ethylcarbamoyloxy group, an N-phenylcarbamoyloxy group, etc. are used.

As the "$C_{1-6}$ alkanoylamino group", for example, an acetamido group, a propionamido group, a butyramido group, a valeramido group, a pivalamido group, etc. are used, as the "$C_{6-10}$ aryl-carbonylamino group", for example, a benzamido group, a naphthamido group, a phthalimido group, etc. are used, as the "$C_{1-10}$ alkoxy-carboxamido group", for example, a methoxy-carboxamido ($CH_3OCONH-$) group, an ethoxycarboxamido group, a tert-butoxycarboxamido group, etc. are used, as the "$C_{6-10}$ aryloxy-carboxamido group", for example, a phenoxycarboxamido ($C_6H_5OCONH-$) group, etc. are used, as the "$C_{7-10}$ aralkyloxy-carboxamido group", for example, a benzyloxycarboxamido ($C_6H_5CH_2OCONH-$) group, a benzhydryloxycarboxamido group, etc. are used, as the "$C_{1-10}$ alkoxy-carbonyloxy group", for example, a methoxycarbonyloxy group, an ethoxycarbonyloxy group, an n-propoxycarbonyloxy group, an isopropoxycarbonyloxy group, an n-butoxycarbonyloxy group, a tert-butoxycarbonyloxy group, an n-pentyloxycarbonyloxy group, an n-hexyloxycarbonyloxy group, etc. are used, as the "$C_{6-10}$ aryloxy-carbonyloxy group", for example, a phenoxycarbonyloxy group, a naphthyloxycarbonyloxy group, etc. are used, as the "$C_{7-19}$ aralkyloxy-carbonyloxy group", for example, a benzyloxycarbonyloxy group, a 1-phenylethyloxycarbonyloxy group, a 2-phenylethyloxycarbonyloxy group, a benzhydryloxycarbonyloxy group, etc. are used, and as the "$C_{3-10}$ cycloalkyloxy-carbonyloxy group", for example, a cyclopropyloxycarbonyloxy group, a cyclohexyloxycarbonyloxy group, etc. are used.

As the "ureido group optionally having substituents", for example, a ureido group optionally substituted by 1 to 3 (preferably 1 or 2) substituents selected from a $C_{1-4}$ alkyl group (e.g., a methyl group, an ethyl group, etc.), a phenyl group, etc. are used, and, for example, a ureido group, a 1-methylureido group, a 3-methylureido group, a 3,3-dimethylureido group, a 1,3-dimethylureido group, a 3-phenylureido group, etc. are used.

When a heterocyclic group, a heterocyclic oxy group, a heterocyclic thio group, a heterocyclic sulfinyl group, a heterocyclic sulfonyl group or a heterocyclic oxycarbonyl group is used as the "substituents" of the "aliphatic hydrocarbon group optionally having substituents", the heterocyclic group represents a group formed by excluding one hydrogen atom that binds to the heterocycle, and it represents, for example, a 5- to 8-membered cyclic (preferably 5- or 6-membered cyclic) group containing 1 to a few, preferably 1 to 4 hetero atoms such as a nitrogen atom (optionally oxidized), an oxygen atom, a sulfur atom, etc., or its condensed cyclic group. As these heterocyclic groups, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxinyl group, a dioxolyl group, a quinolyl group, a pyrido[2,3-d]pyrimidyl group, a 1,5-, 1,6-, 1,7-, 1,8-, 2,6- or 2,7-naphthyridyl group, a thieno[2,3-d] pyridyl group, a benzopyranyl group, a tetrahydrofuryl group, a tetrahydropyranyl group, a dioxolanyl group, a dioxanyl group, etc. are used.

These heterocyclic groups may be substituted at substitutable positions by 1 to 3 substituents selected from a $C_{1-4}$ alkyl (e.g., methyl, ethyl, etc.), a hydroxy, an oxo, a $C_{1-4}$ alkoxy (e.g., methoxy, ethoxy, etc.), and the like.

As the "$C_{6-10}$ aryl group" of the "$C_{6-10}$ aryl group optionally having substituents", for example, a phenyl group, a naphthyl group, etc. are used. The $C_{6-10}$ aryl group may be substituted at a substitutable position by a substituent selected from those exemplified as the "substituent" (except for an optionally substituted $C_{6-10}$ aryl group) of the "aliphatic hydrocarbon group optionally having substituents" described above. Such substituent is substituted at a substitutable position of the $C_{6-10}$ aryl group, wherein such substituent is not limited to a single substituent, but the same or different, more than one (2 to 4) substituents may be used.

In the "aliphatic hydrocarbon group optionally having substituents", the substituent together with the aliphatic hydrocarbon group may form an optionally substituted condensed ring group, and as such condensed ring group, an indanyl group, a 1,2,3,4-tetrahydronaphthyl group, etc. are used. This condensed ring group may be substituted at a substitutable position by a substituent selected from those exemplified as the "substituent" of the "aliphatic hydrocarbon optionally having substituents" described above. Such substituent is substituted at a substitutable position of the condensed ring group, wherein the substituent is not limited to a single substituent, but the same or different, more than one (2 to 4) substituents may be used.

As R, $R^1$, $R^{1a}$, $R^{1b}$ and $R^{1c}$, for example, a lower alkyl group having 1 to 6 carbon atoms (e.g., a methyl group, an ethyl group, an n-propyl group, an isopropyl group, an n-butyl group, an isobutyl group, a tert-butoxycarbonylmethyl group, a hydroxyethyl group and the like) optionally having substituents, etc., are used. Of these, a methyl group, an ethyl group, an n-propyl group, an isopropyl group, an n-butyl group, an isobutyl group, etc. are preferably used. Particularly, for example, a methyl group, an ethyl group, an n-propyl group and the like, are preferable, and particularly, an ethyl group, etc. is preferable.

As $R^2$ and $R^{2a}$, for example, a hydrogen atom, a lower alkyl group having 1 to 6 carbon atoms (e.g., a methyl group, an ethyl group, an n-propyl group, an isopropyl group, an n-butyl group, an isobutyl group, a tert-butoxycarbonylmethyl group, a hydroxyethyl group and the like), etc. are preferably used, and of these, a hydrogen atom, a methyl group, etc. are particularly preferably used and particularly, a hydrogen atom, etc. are preferably used.

As the "aromatic hydrocarbon group" of the "aromatic hydrocarbon group optionally having substituents" represented by Ar and $Ar^a$, an aromatic hydrocarbon group having 6 to 14 carbon atoms (e.g., a phenyl group, a naphthyl group, a biphenyl group, an anthryl group, an indenyl group and the like) and the like are preferable, and particularly for example, an aryl group having 6 to 10 carbon atoms (e.g., phenyl, naphthyl groups etc.) and the like are preferable and, of these, a phenyl group and the like are particularly preferable.

As the "substituent" of the "aromatic hydrocarbon group optionally having substituents" represented by Ar and $Ar^a$, for example, a halogen atom (e.g., fluorine, chlorine, bromine, iodine and the like), a lower $(C_{1-4})$ alkyl group (e.g., a methyl group, an ethyl group, a propyl group, a butyl group and the like), a lower $(C_{1-4})$ alkoxy group (e.g., a methoxy group, an ethoxy group, a propoxy group, a butoxy group and the like), a lower $(C_{1-4})$ alkoxycarbonyl group (e.g., a methoxycarbonyl group, an ethoxycarbonyl group, a propoxycarbonyl group, a butoxycarbonyl group and the like), a carboxyl group, a nitro group, a cyano group, a hydroxyl group, an acylamino group (e.g., an alkanoylamino group having 1 to 4 carbon atoms such as an acetylamino group, a propionylamino group, a butyrylamino group and the like), a cycloalkyl group having 3 to 6 carbon atoms (e.g., a cyclopropyl group, a cyclopentyl group and the like), an aryl group having 6 to 10 carbon atoms (e.g., a phenyl group, a naphthyl group, an indenyl group and the like), a halogeno-lower $(C_{1-4})$ alkyl group (e.g., a trifluoromethyl group, a trifluoroethyl group and the like), a halogeno-lower $(C_{1-4})$ alkoxy group (e.g., a trifluoromethoxy group, a 1,1,2,2-tetrafluoroethoxy group, a 2,2,3,3,3-pentafluoropropoxy group and the like), a lower $(C_{1-4})$ alkylthio group (e.g., a methylthio group, an ethylthio group, a propionylthio group and the like), a lower $(C_{1-4})$ alkylsulfonyl group (e.g., a methanesulfonyl group, an ethanesulfonyl group, a propanesulfonyl group and the like), a lower $(C_{1-4})$ alkanoyl group (e.g., a formyl group, an acetyl group, a propionyl group and the like), a 5-membered aromatic heterocyclic group (e.g., a 1,2,3-triazolyl group, a 1,2,4-triazolyl group, a tetrazolyl group, a thiazolyl group, an isothiazolyl group, an oxazolyl group, an isoxazolyl group, a thiadiazolyl group, a thienyl group, a furyl group and the like), a carbamoyl group, a lower $(C_{1-4})$ alkyl-carbamoyl group (e.g., a methylcarbamoyl group, a dimethylcarbamoyl group, a propionylcarbamoyl group and the like), a lower $(C_{1-4})$ alkoxy-carbonyl-lower $(C_{1-4})$ alkyl-carbamoyl group (e.g., a butoxycarbonylmethylcarbamoyl group, an ethoxycarbonylmethylcarbamoyl group and the like), a 1,3-diacylguanidino-lower $(C_{1-4})$ alkyl group (e.g., 1,3-diacetylguanidinomethyl, 1,3-bis-tert-butoxycarbonyl-guanidinomethyl and the like) and the like are used, and a halogen atom (e.g., fluorine, chlorine, bromine, iodine atoms and the like), a lower $(C_{1-4})$ alkyl group (e.g., a methyl group, an ethyl group, a propyl group, a butyl group and the like) and the like are preferably used, and a fluorine atom, a chlorine atom and a methyl group are more preferably used.

These substituents are substituted at substitutable positions of the aromatic hydrocarbon group, and the number of the substituents is preferably 1 to 5, more preferably 1 to 3, most preferably 1 or 2. When two or more of such substituents are present, they may be the same or different.

Typically, as Ar and $Ar^a$, for example, a phenyl group, a halogenophenyl group, a lower $(C_{1-4})$ alkylphenyl group, a lower $(C_{1-4})$ alkoxyphenyl group, a lower $(C_{1-4})$ alkoxycarbonylphenyl group, a carboxylphenyl group, a nitrophenyl group, a cyanophenyl group, a halogeno-lower $(C_{1-4})$ alkylphenyl group, a halogeno-lower $(C_{1-4})$ alkoxyphenyl group, a lower $(C_{1-4})$ alkanoylphenyl group, a 5-membered aromatic heterocycle-substituted phenyl group, a lower $(C_{1-4})$ alkoxy-carbonyl-lower $(C_{1-4})$ alkyl-carbamoylphenyl group, 1,3-diacylguanidino-lower $(C_{1-4})$ alkylphenyl group, a halogen- and lower $(C_{1-4})$ alkyl-substituted phenyl group, a halogen- and lower $(C_{1-4})$ alkoxycarbonyl-substituted phenyl group, a halogen- and cyano-substituted phenyl group, a halogen- and 5-membered aromatic heterocycle-substituted phenyl group, a halogen- and lower $(C_{1-4})$ alkoxy-carbonyl-lower $(C_{1-4})$ alkyl-carbamoyl-substituted phenyl group and the like are used.

As Ar and $Ar^a$, a halogenophenyl group, a lower $(C_{1-4})$ alkylphenyl group, a halogen- and lower $(C_{1-4})$ alkoxycarbonyl-substituted phenyl and the like are preferably used.

As Ar and $Ar^a$, a group represented by the formula:

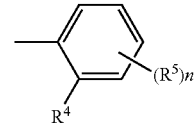

wherein $R^4$ and $R^5$ are the same or different and each represents a halogen atom or a lower alkyl group, and n is an integer of 0 to 2, are more preferable, in which a group wherein at least one of $R^4$ and $R^5$ is a halogen atom is still more preferable.

As the halogen atom represented by $R^4$ and $R^5$, a fluorine atom or a chlorine atom is preferable.

As the halogenophenyl group, for example, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorohenyl and the like are used.

As the lower ($C_{1-4}$) alkylphenyl group, for example, a 2-ethylphenyl group, a 2,6-diisopropylphenyl group and the like are preferably used, and as the lower ($C_{1-4}$) alkoxyphenyl group, for example, a 4-methoxyphenyl and the like are preferably used.

As the lower ($C_{1-4}$) alkoxy-carbonylphenyl group, for example, a 2-ethoxycarbonylphenyl group, a 2-methoxycarbonyl-phenyl group, a 4-methoxycarbonylphenyl group and the like are preferably used, and as the halogeno-lower ($C_{1-4}$) alkylphenyl group, for example, a 2-trifluoromethylphenyl group and the like are preferably used, and as the halogeno-lower ($C_{1-4}$) alkoxyphenyl group, for example, a 2-trifluoromethoxyphenyl group, a 4-(2,2,3,3,3-pentafluoropropoxy)phenyl group and the like are preferably used.

As the lower ($C_{1-4}$) alkanoylphenyl group, for example, a 2-acetylphenyl group and the like are preferably used, and as the 5-membered aromatic heterocycle-substituted phenyl group, for example, a 4-(2H-1,2,3-triazol-2-yl)phenyl group, a 4-(2H-tetrazol-2-yl)phenyl group, a 4-(1H-tetrazol-1-yl)phenyl group, a 4-(1H-1,2,3-triazol-1-yl)phenyl group and the like are preferably used, and as the lower ($C_{1-4}$) alkoxy-carbonyl-lower ($C_{1-4}$) alkyl-carbamoylphenyl group, for example, a 4-(N-ethoxycarbonylmethylcarbamoyl) phenyl group and the like are preferably used, and as the 1,3-diacylguanidino-lower ($C_{1-4}$) alkylphenyl group, for example, a 4-(1,3-bis-tert-butoxycarbonylguanidinomethyl) phenyl group and the like are preferably used.

As the phenyl group substituted by halogen and lower ($C_{1-4}$) alkyl, for example, a 2-fluoro-4-methylphenyl group, a 2-chloro-4-methylphenyl group, a 4-fluoro-2-methylphenyl group and the like are preferably used, and as the phenyl group substituted by halogen and lower ($C_{1-4}$) alkoxycarbonyl, for example, a 2-chloro-4-methoxycarbonylphenyl group and the like are preferably used, and the phenyl group substituted by halogen and cyano, a 2-chloro-4-cyanophenyl group and the like are preferably used, and as the phenyl group substituted by halogen and 5-membered aromatic heterocycle, for example, a 2-fluoro-4-(1H-1,2,4-triazol-1-yl)phenyl group and the like are preferably used, and as the phenyl group substituted by halogen and lower ($C_{1-4}$) alkoxy-carbonyl-lower ($C_{1-4}$) alky-carbamoyl, for example, a 2-chloro-4-(N-tert-butoxycarbonylmethylcarbamoyl)-phenyl group, a 2-chloro-4-(N-ethoxycarbonylmethylcarbamoyl)-phenyl group and the like are preferably used.

More specifically, as Ar and $Ar^a$, a phenyl group, a phenyl group substituted by 1 to 3 (particularly 1 or 2) halogen atoms (e.g., a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 4-bromo-2-fluorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 2,3,4-trifluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferable. Of these, a phenyl group substituted by 1 to 3 (particularly 1 or 2) halogen atoms (e.g., a 2,3-dichlorophenyl group, a 2,4-difluorophenyl group, a 2,4-dichlorophenyl group, a 2,6-dichlorophenyl group, a 2-fluorophenyl group, a 2-chlorophenyl group, a 3-chlorophenyl group, a 2-chloro-4-fluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferable. Particularly, a 2,4-difluorophenyl group, a 2-chlorophenyl group, a 2-chloro-4-fluorophenyl group, a 2-chloro-4-methylphenyl group and the like are preferable, and a 2,4-difluorophenyl group, a 2-chloro-4-fluorophenyl group and the like are preferable.

In this specification, the ring $A^1$ represents a cycloalkene optionally substituted by 1 to 4 substituents selected from the group consisting of (i) an aliphatic hydrocarbon group optionally having substituents, (ii) an aromatic hydrocarbon group optionally having substituents, (iii) a group represented by the formula —$OR^1$ (wherein $R^1$ is as defined above) and (iv) a halogen atom, and a cycloalkene optionally substituted by 1 to 4 substituents selected from the group consisting of (i) an aliphatic hydrocarbon group optionally having substituents, (ii) an aromatic hydrocarbon group optionally having substituents and (iv) a halogen atom are preferable.

In this specification, the ring $A^2$ represents a cycloalkene substituted by 1 to 4 substituents selected from the group consisting of (i) an aliphatic hydrocarbon group optionally having substituents, (ii) an aromatic hydrocarbon group optionally having substituents, (iii) a group represented by the formula —$OR^1$ (wherein $R^1$ is as defined above) and (iv) a halogen atom, and a cycloalkene substituted by 1 to 4 substituents selected from the group consisting of (i) an aliphatic hydrocarbon group optionally having substituents, (ii) an aromatic hydrocarbon group optionally having substituents and (iv) a halogen atom are preferable.

These substituents are substituted on substitutable carbon atoms in the ring $A^1$ and ring $A^2$, and when the ring $A^1$ or $A^2$ is substituted by two or more of such substituents, the substituents may be the same or different. A single carbon atom may be substituted by two substituents and different carbon atoms may be substituted by two or more substituents.

As the "aliphatic hydrocarbon group optionally having substituents" as a substituent on the ring $A^1$ and ring $A^2$, for example, the same those as the "aliphatic hydrocarbon group optionally having substituents" represented by R, $R^1$, $R^{1a}$, $R^{1b}$ and $R^{1c}$ described above may be used.

As the "aromatic hydrocarbon group optionally having substituents" as a substituent on the ring $A^1$ and ring $A^2$, for example, the same those as the "aromatic hydrocarbon group optionally having substituents" represented by Ar and $Ar^a$ described above may be used.

As the "heterocyclic group optionally having substituents" as a substituent on the ring $A^1$ and ring $A^2$, for example, those similar to the "heterocyclic group" which is a "substituent" on the "aliphatic hydrocarbon group optionally having substituents" represented by R, $R^1$, $R^{1a}$, $R^{1b}$ and $R^{1c}$ described above may be used.

As the substituents for the ring $A^1$ and ring $A^2$, 1 or 2 $C_{1-6}$ alkyl groups (e.g., a $C_{1-4}$ alkyl group such as a methyl group, a tert-butyl group, etc.), a phenyl group, a halogen atom (e.g., fluorine, chlorine, bromine, iodine, etc.), etc. are preferably used.

The group represented by the formula:

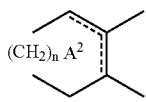

wherein n is as defined above, representes a group represented by the formula:

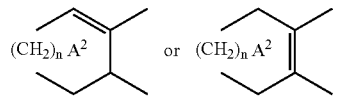

wherein n is as defined above, preferably a group represented by the formula:

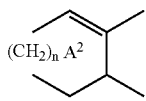

wherein n is as defined above.

The group represented by the formula:

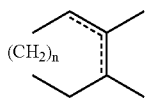

wherein n is as defined above, represents a group represented by the formula:

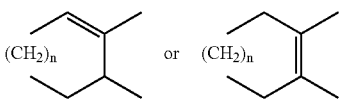

wherein n is as defined above, preferably a group represented by the formula:

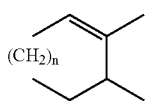

wherein n is as defined above, and a group represented by the formula:

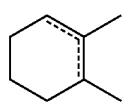

represents a group represented by the formula:

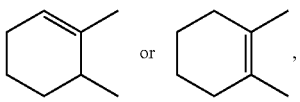

preferably a group represented by the formula:

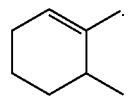

As the integer of 1 to 4 represented by n, 1 to 3 is preferable and 2 is particularly preferable.

As the compound represented by the formula (Iaa), the compound represented by the formula (Ibb) is preferable, and as the compound represented by the formula (Ia), the compound represented by the formula (Ib) is preferable.

As the compound represented by the formula (Ibb), the compound represented by the formula (Inn) is preferable, and as the compound represented by the formula (Ib), the compound represented by the formula (In) is preferable.

As the compounds represented by the formulas (Ibb) and (Ib), a compound wherein $R^1$ is a lower alkyl group optionally having substituents, $R^2$ is a hydrogen atom or a lower alkyl group, Ar is a phenyl group optionally having substituents, and n is 1, 2 or 3 is preferable, and a compound wherein $R^1$ is a lower alkyl group optionally having substituents, $R^2$ is a hydrogen atom, Ar is a phenyl group substituted by a halogen atom, and n is 2 is more preferable.

As the compounds represented by the formulas (Icc) and (Ic), a compound wherein Ar is a phenyl group optionally having substituents, and n is 2 is preferable.

When the compounds represented by the formulas (I), (Iaa), (Ibb), (Icc), (Ia), (Ib), (Ic), (Id), (Ie), (If) and (Ig) have stereoisomers, all such stereoisomers and mixtures thereof are encompassed in the present invention.

When a compound represented by the formula (Iaa) is a compound represented by the formula (Icc) or (Inn), when a compound represented by the formula (Ia) is a compound represented by the formula (Ic) or (In), when a compound represented by the formula (Ie) is a compound represented by the formula (Ik) or (Ip), when a compound represented by the formula (Id) is a compound represented by the formula (Ir), and when a compound represented by the formula (Ig) is a compound represented by the formula (It), then each compound can exist as an optical isomer with regard to the asymmetric carbon atom in a cycloalkene or cyclohexene ring, and any of such optical isomers and mixtures thereof are included in the present invention.

A compound represented by the formula (I) or (Ia) is used, which is specifically the compound in Reference Example B to be mentioned below, and the like. Of such compounds, (A) d-ethyl 6-[N-(2,4-difluorophenyl)sulfamoyl]-1-cyclohexene-1-carboxylate, (B) ethyl 6-[N-(2-chlorophenyl)sulfamoyl]-1-cyclohexene-1-carboxylate, (C) ethyl 6-[N-(2-chloro-4-methylphenyl)sulfamoyl]-1-cyclohexene-1-carboxylate, (D) d-ethyl 6-[N-(2-chloro-4-fluorophenyl)sulfamoyl]-1-cyclohexene-1-carboxylate and salts thereof are preferable.

The compounds (I), (Iaa), (Ia), (Ib), (Ic), (Id), (Ie), (If), (Ig), (Ibb) and (Icc) (hereinafter to be simply referred to as an inventive Compound), which is used for the composition of the present invention, may be converted into a salt with an inorganic base, organic base, inorganic acid, organic acid, basic or acidic amino acid, and the like. The salt with an inorganic base may, for example, be used an alkaline metal salt such as sodium and potassium salts, etc.; an alkaline earth metal salt such as calcium and magnesium salts, etc.; aluminum and ammonium salts, and the like, and a salt with an organic base may, for example, be used a salt with trimethylamine, triethylamine, pyridine, picoline, ethanolamine, diethanolamine, triethanolamine, dicyclohexylamine, N,N'-dibenzylethylenediamine, etc. A salt with an inorganic acid may, for example, be used a salt with hydrochloric acid, hydrobromic acid, nitric acid, sulfuric acid, phosphoric acid, etc., and a salt with an organic acid may, for example, be used a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. A salt with a basic amino acid may, for example, be used a salt with arginine, lysine, ornithine, etc., and a salt with acidic amino acid may, for example, be used a salt with aspartic acid, glutamic acid, etc.

A prodrug for an inventive Compound or a salt thereof is a compound which is converted into an inventive Compound under a physiological condition in vivo as a result of a reaction with an enzyme, gastric acid etc., thus a compound undergoing an enzymatic oxidation, reduction, hydrolysis etc. to convert into an inventive Compound and a compound subjected to hydrolysis and the like by gastric acid etc. to convert into an inventive Compound. A prodrug for an inventive Compound may, be a compound obtained by subjecting an amino group in an inventive Compound to an acylation, alkylation or phosphorylation (e.g., a compound obtained by subjecting an amino group in an inventive Compound to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in an inventive Compound to an acylation, alkylation, phosphorylation and boration (e.g., a compound obtained by subjecting a hydroxy group in an inventive Compound to an acetylation, palmitoylation, propanoylation, pivaloylation, succinylation, fumarylation, alanylation, dimethylaminomethylcarbonylation, etc.); a compound obtained by subjecting a carboxyl group in an inventive Compound to an esterification or amidation (e.g., a compound obtained by subjecting a carboxyl group in an inventive Compound to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification and methylamidation, etc.) and the like. Any of these compounds can be produced from an inventive Compound by a method known per se.

A prodrug for an inventive Compound may also be one which is converted into an inventive Compound under a physiological condition, such as those described in "IYAKUHIN no KAIHATSU (Development of Pharmaceuticals)", Vol. 7, Design of Molecules, p. 163-198, Published by HIROKAWA SHOTEN (1990).

The inventive Compound, a salt thereof and a prodrug thereof can be produced according to a method known per se, for example, a production method described in WO99/46242 or a method analogous thereto.

The inventive Compound, a salt thereof and a prodrug thereof may be a hydrate or non-hydrate.

The inventive Compound, a salt thereof and a prodrug thereof may be labeled with an isotope (e.g., $^3$H, $^{14}$C, $^{35}$S, $^{125}$I etc.) and the like.

The nonionic surfactant to be used for the pharmaceutical composition of the present invention is, for example, a higher alcohol ethyleneoxide adduct, an alkylphenol ethyleneoxide adduct, a fatty acid ethyleneoxide adduct, a polyhydric alcohol fatty acid ester ethyleneoxide adduct, a higher alkylamine ethyleneoxide adduct, a fatty acid amide ethyleneoxide adduct, an ethyleneoxide adduct of fat and oil, a polypropylene glycol ethyleneoxide adduct, a fatty acid ester of glycerol, a fatty acid ester of pentaerythritol, a fatty acid ester of sorbitol or sorbitan, a fatty acid ester of sucrose, an alkyl ether of polyhydric alcohol, a fatty acid amide of alkanolamines, a polyoxyethylene castor oil derivative and the like.

Of the nonionic surfactants, for example, polyoxyethylene castor oil derivatives such as polyoxyethylene castor oil (polyethoxylated castor oil), polyoxyethylene hydrogenated castor oil (polyethoxylated hydrogenated castor oil) and the like are preferably used.

As the polyoxyethylene castor oil (polyethoxylated castor oil), polyoxyethylene glycerol triricinoleate 35 (Polyoxy 35 Castor Oil, trademark Cremophor EL or EL-P, BASF Japan Ltd.) and the like are particularly preferable.

As the polyoxyethylene hydrogenated castor oil (polyethoxylated hydrogenated castor oil), polyoxyethylene hydrogenated castor oil 50 (Polyoxyethylene Hydrogenated Castor Oil 50), polyoxyethylene hydrogenated castor oil 60 (Polyoxyethylene Hydrogenated Castor Oil 60) and the like are particularly preferable.

The pharmaceutical composition of the present invention may contain a surfactant other than the nonionic surfactants, and specifically, may contain an anionic surfactant, a cationic surfactant and an amphoteric surfactant.

As the anionic surfactant, for example, sulfuric acid esters (e.g., a salt of higher alcohol sulfuric acid ester, a salt of higher alkyl ether sulfuric acid ester, a sulfated oil, a sulfated fatty acid ester, a sulfated fatty acid, a sulfated olefin), sulfonic acid salts (e.g., sodium alkylbenzenesulfonate, oil soluble alkylbenzenesulfonic acid salt, α-olefinsulfonic acid salt, Igepon T type, Aerosol OT type), phosphoric acid esters (e.g., a salt of phosphoric acid ester of higher alcohol ethyleneoxide adduct), a salt of dithiophosphoric acid ester and the like are used.

As the cationic surfactant, for example, amine salt type cationic surfactants (e.g., an amine salt type cationic surfactant made from higher alkylamine, an amine salt type cationic surfactant made from lower or higher alkylamine), quaternary ammonium salt type cationic surfactants (e.g., a quaternary ammonium salt type cationic surfactant made from higher alkylamine, a quaternary ammonium salt type surfactant made from lower or higher alkylamine) and the like are used.

As the amphoteric surfactant, for example, an amino acid type amphoteric surfactant, a betaine type amphoteric surfactant and the like are used.

The pharmaceutical composition of the present invention may further contain ethanol, benzyl alcohol or dimethylacetamide. Of these, ethanol is preferable.

When the pharmaceutical composition of the present invention is an injection, the pH is desirably adjusted to about 3-10, preferably about 4-9, more preferably about 4-7.

The pharmaceutical composition of the present invention can be produced by mixing compound (I), a salt thereof or a prodrug thereof (hereinafter to be simply abbreviated as compound (I)), a nonionic surfactant, and where necessary, an additive such as ethanol, other surfactant and the like by a known method.

The pharmaceutical composition of the present invention may be a solution itself thus obtained, or a solution obtained by dissolving the obtained powder in a suitable solvent, or, where desired, may contain a pharmacologically acceptable carrier as appropriate.

A pharmaceutical composition of the present invention has low toxicity and compound (I) can be administered safely by admixing with, for example, a pharmacologically acceptable carrier according to a method known per se to give a pharmaceutical composition, such as tablets (inclusive of sugar-coated tablets and film-coated tablets), powders, granules, capsules, (inclusive of soft capsules), liquids, injections, suppositories, sustained release agents and the like, for oral or parenteral (e.g., topical, rectal or intravenous administration) administration. The pharmaceutical composition of the present invention is preferably an injection, more preferably a non-emulsified composition or clear injection.

In the present invention, by the "non-emulsified composition" is meant a composition other than an emulsion, or a composition which is not an O/W type emulsion or a W/O type emulsion. In other words, when two solutions are mixed, phase separation, or emulsification wherein one phase is dispersed in the other phase in a fine particle state, does not occur, but a composition having a single phase, which is a uniform mixture.

In the present invention, "being clear" means a state free of cloudiness by visual oil drop or particles.

As the pharmacologically acceptable carrier usable for the production of the preparation of the present invention, there are mentioned various conventional organic or inorganic carriers as a material for the preparation. Examples thereof include excipients, lubricants, binders and disintegrators for solid preparations, and solvents, solubilizers, suspending agents, isotonic agents, buffers, soothing agents, and the like for liquid preparations. Where necessary, conventional additives such as antiseptics, antioxidants, coloring agents, sweeteners, absorbents, moistening agents and the like can be used appropriately in suitable amounts.

As the excipient, there are mentioned, for example, lactose, sucrose, D-mannitol, starch, corn starch, crystalline cellulose, light anhydrous silicic acid and the like.

As the lubricant, there are mentioned, for example, magnesium stearate, calcium stearate, talc, colloidal silica and the like.

As the binder, there are mentioned, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

As the disintegrator, there are mentioned, for example, starch, carboxymethylcellulose, carboxymethylcellulose calcium, sodium carboxymethyl starch, L-hydroxypropylcellulose and the like.

As the solvent, there are mentioned, for example, water for injection, alcohol, propylene glycol, Macrogol, sesame oil, corn oil, olive oil and the like.

As the solubilizer, there are mentioned, for example, polyethylene glycol, propylene glycol, D-mannitol, benzyl benzoate, ethanol, tris-aminomethane, cholesterol, triethanolamine, sodium carbonate, sodium citrate and the like.

As the suspending agent, there are mentioned, for example, surfactants such as stearyl triethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like.

As the isotonic agent, there are mentioned, for example, glucose, D-sorbitol, sodium chloride, glycerine, D-mannitol and the like.

As the buffer, there are mentioned, for example, buffers such as phosphate, acetate, carbonate, citrate etc., and the like.

As the soothing agent, there are mentioned, for example, benzyl alcohol and the like.

As the antiseptic, there are mentioned, for example, p-oxybenzoates, chlorobutanol, benzyl alcohol, phenethyl alcohol, dehydroacetic acid, sorbic acid and the like.

As the antioxidant, there are mentioned, for example, sulfite, ascorbic acid, $\alpha$-tocopherol and the like.

Particularly, when the pharmaceutical composition of the present invention is used as an injection, a carrier for injection to be used is exemplified by a solvent, a solubilizer, a suspending agent, an isotonic agent, a buffer, a soothing agent and the like. Examples of the solvent include water for injection, physiological saline, Ringer's solution and the like. Examples of the solubilizer include polyethylene glycol, propylene glycol, D-mannitol, benzyl benzoate, trisaminomethane, cholesterol, triethanolamine, sodium carbonate, sodium citrate and the like. Examples of the isotonic agent include glucose, D-sorbitol, sodium chloride, glycerin, D-mannitol and the like. Examples of the buffer include buffers such as phosphate, acetate, carbonate, citrate and the like, and the like. Examples of the soothing agent include benzyl alcohol and the like. Examples of the pH adjusting agent include hydrochloric acid, phosphoric acid, citric acid, sodium hydroxide and the like.

The composition for injection of the present invention thus obtained can be freeze-dried in an aseptically treated in a freeze dryer and preserved in a powder state, or can be sealed in a container for injection (e.g., ampoule) and preserved.

In addition, the pharmaceutical composition of the present invention can be diluted with the aforementioned carrier for injection when in use.

The content of compound (I) in the pharmaceutical composition of the present invention varies depending on the form of the preparation, but it is generally about 0.01-about 99 wt %, preferably about 0.1-about 50 wt %, more preferably about 0.5-about 20 wt %, of the whole preparation.

The content of nonionic surfactant in the pharmaceutical composition of the present invention varies depending on the form of the preparation, but it is generally about 1-about 99.99 wt %, preferably about 10-about 90 wt %, more preferably about 10-about 70 wt %, of the whole preparation.

The content of ethanol, benzyl alcohol or dimethylacetamide in the pharmaceutical composition of the present invention varies depending on the form of the preparation, but it is generally about 1-about 99.99 wt %, preferably about 10-about 90 wt %, more preferably about 30-about 90 wt %, of the whole preparation.

The mixing ratio (weight ratio) of nonionic surfactant and ethanol in the pharmaceutical composition of the present invention is not particularly limited, and is, for example, nonionic surfactant:ethanol=about 0.01-99.99:99.99-0.01, preferably about 1-99:99-1, more preferably about 10-90: 90-10 and the like. More preferably, nonionic surfactant: ethanol=about 10-80:90-20, about 50-80:50-20 and the like, and particularly, about 20:80, about 65:35 and the like are preferable.

The content of cyclodextrin derivative readily soluble in water in the pharmaceutical composition of the present invention varies depending on the form of the preparation, but it is generally about 1-about 99.99 wt %, preferably about 10-about 99.99 wt %, more preferably about 20-about 97 wt %, particularly preferably about 50-about 97 wt %, of the whole preparation.

The content of other additive in the pharmaceutical composition of the present invention varies depending on the form of the preparation, but it is generally about 1-about 99.99 wt %, preferably about 10-about 90 wt %, more preferably about 10-about 70 wt %, of the whole preparation.

The pharmaceutical composition of the present invention may be a pharmaceutical composition comprising compound (I), a nonionic surfactant and a cyclodextrin derivative readily soluble in water. In this case, the content of each component of compound (I), a nonionic surfactant and a cyclodextrin derivative readily soluble in water is the same as in the aforementioned range.

When the pharmaceutical composition of the present invention containing a complex of compound (I) and a cyclodextrin derivative readily soluble in water is used as an injection, pyrogen (e.g., endotoxin) can be removed efficiently by filtering a composition containing the above-mentioned various components with a hollow fiber ultra filtration membrane having a fractionation molecular weight of about 1,000-8,000, preferably about 2,000-7,000, more preferably 3,000-7,000, particularly preferably about 6,000.

As such hollow fiber ultra filtration membrane, commercially available ones can be used as appropriate. For example, hollow fiber ultra filtration membrane SIP-0013 having a fractionation molecular weight of 6,000 and manufactured by Asahi Kasei Corporation; pencil type module ($20_\phi \times 130$ mm) and the like can be used.

The pore size of the hollow fiber ultra filtration membrane is generally about 10-100 angstrom, preferably about 20-60 angstrom.

The number of the hollow fiber ultra filtration membrane to be used may be one, but two or more (e.g., 2-3, preferably 2) may be used by directly connecting them. Particularly, a combination of a hollow fiber ultra filtration membrane having a fractionation molecular weight of 6,000 and a hollow fiber ultra filtration membrane having a fractionation molecular weight of 3,000 is preferable.

The hollow fiber ultra filtration membrane is washed before use with, for example, sodium hypochlorite solution and the like for about 1-30 hr, by immersion, and then with aqueous solution for injection free of pyrogen until the pH of the solution after passage becomes about 7.0.

The pressure for ultra filtration is set for generally about 0.05-1.0 kg/cm$^3$, preferably about 0.1-0.5 kg/cm$^3$. The filtration can be done at room temperature, preferably under aseptic conditions.

The content of pyrogen in the present composition for injection is generally not more than about 100 EU/g, preferably not more than about 50 EU/g, particularly preferably not more than about 30 EU/g.

The content of pyrogen in the present composition for injection can be quantitatively determined by a method known per se. More specifically, endotoxin concentration (EU) can be determined from absorbance at 405 nm using an endotoxin measurement reagent such as TOXICOLOR system Et-2 set (standard endotoxin) and TOXICOLOR system LS-20 set manufactured by SEIKAGAKU CORPORATION, and the like.

The present composition for injection thus obtained can be preserved as a powder by freeze-drying in an aseptically treated freeze dryer, or preserved after sealing as it is in a container for injection (e.g., ampoule).

The cyclodextrin derivative readily soluble in water to be used for the pharmaceutical composition of the present invention may be a commercially available one or can be produced by a method known per se.

The cyclodextrin derivative readily soluble in water to be used is preferably a compound wherein hydrogen(s) of a part of or all hydroxyl groups at the 2-, 3- and 6-positions of glucose of cyclic oligosaccharide consisting of 6-12 glucose units is(are) substituted by other functional group (e.g., a dihydroxyalkyl group, a saccharide residue, a hydroxyalkyl group and the like) and the like.

Said cyclodextrin derivative readily soluble in water shows solubility in water of not less than about 50 mg/ml, preferably not less than about 100 mg/ml.

Preferable examples of the cyclodextrin derivative readily soluble in water include a compound represented by the formula:

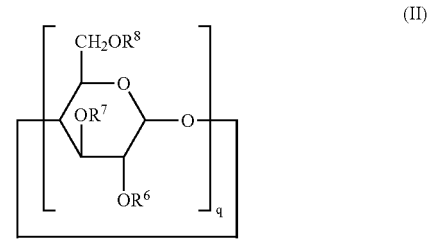

wherein q is an integer of 6-12, and R$^6$, R$^7$ and R$^8$ are the same or different in individual repeating unit and each is a hydrogen atom, a dihydroxyalkyl group, a saccharide residue or a hydroxyalkyl group, and at least one of R$^6$, R$^7$ and R$^8$ is a dihydroxyalkyl group, a saccharide residue or a hydroxyalkyl group. Concrete examples thereof include ether derivatives at hydroxyl group of $\alpha$-CyD (q=6), $\beta$-CyD (q=7), $\gamma$-CyD (q=8), $\delta$-CyD (q=9) and the like. Of these, an ether derivative at hydroxyl group of $\beta$-CyD is preferable (in the present specification, CyD means cyclodextrin).

The dihydroxyalkyl group represented by R$^6$-R$^8$ is, for example, dihydroxy-C$_{1-6}$ alkyl group (e.g., dihydroxymethyl, 2,2-dihydroxyethyl, 2,2-dihydroxypropyl, 2,2-dihydroxypentyl, 2,2-dihydroxyhexyl and the like), preferably dihydroxy-C$_{1-4}$ alkyl group (e.g., dihydroxymethyl, 2,2-dihydroxyethyl, 2,2-dihydroxypropyl and the like).

The saccharide residue represented by R$^6$-R$^8$ is, for example, C$_{3-24}$ saccharide residue (erythrosyl, threosyl, arabinosyl, ribosyl, glucosyl, galactosyl, glycero-gluco-heptosyl, maltosyl, lactosyl, maltotriosyl, dimaltosyl and the like), preferably C$_{6-24}$ saccharide residue (e.g., glucosyl, galactosyl, glycero-gluco-heptosyl, maltosyl, lactosyl, maltotriosyl, dimaltosyl and the like), particularly preferably C$_{6-12}$ saccharide residue (e.g., glucosyl, galactosyl, glycero-gluco-heptosyl, maltosyl, lactosyl and the like).

The hydroxyalkyl group represented by R$^6$-R$^8$ is, for example, hydroxy-C$_{1-6}$ alkyl group (e.g., hydroxymethyl, 2-hydroxyethyl, 2-hydroxypropyl, 2-hydroxypentyl, 2-hydroxyhexyl and the like), preferably hydroxy-$C_{1-4}$ alkyl group (e.g., hydroxymethyl, 2-hydroxyethyl, 2-hydroxypropyl and the like), particularly preferably 2-hydroxypropyl group.

More preferable examples of the cyclodextrin derivative readily soluble in water include a compound represented by the formula (II) wherein at least one of $R^6$-$R^8$ is a saccharide residue or a hydroxyalkyl group, and the rest is hydrogen atom.

A compound (II) wherein at least one of $R^6$-$R^8$ is a saccharide residue, and the rest is hydrogen atom is, for example, glucosyl-α, β, γ, δ-CyD, maltosyl-α, β, γ, δ-CyD, maltotriosyl-α, β, γ, δ-CyD, dimaltosyl-α, β, γ, δ-CyD and the like. Of these, maltosyl-α, β, γ, δ-CyD and glucosyl-α, β, γ, δ-CyD are preferable (in the present specification, α, β, γ, δ-CyD means α-CyD, β-CyD, γ-CyD or δ-CyD). Furthermore, maltosyl-β-CyD (hereinafter to be abbreviated as G2-β-CyD) and glucosyl-β-CyD are particularly preferable.

A compound (II) wherein at least one of $R^6$-$R^8$ is a hydroxyalkyl group, and the rest is hydrogen atom is, for example, hydroxypropyl-α, β, γ, δ-CyD (particularly, 2-hydroxypropyl-α, β, γ, δ-CyD) and the like. Of these, hydroxypropyl-β-CyD (particularly, 2-hydroxypropyl-β-CyD) is more preferable.

The cyclodextrin derivative readily soluble in water to be used for the pharmaceutical composition of the present invention may be a branched cyclodextrin-carboxylic acid. This branched cyclodextrin-carboxylic acid includes its free carboxylic acid, as well as a salt thereof with an alkali metal (e.g., lithium, sodium, potassium and the like), an alkaline earth metal (e.g., calcium, magnesium and the like) and the like. These branched cyclodextrin-carboxylic acids can be used alone or in combination thereof, or as mixtures of their free carboxylic acids and salts thereof.

The branched cyclodextrin-carboxylic acid is a cyclodextrin having an organic group containing at least one carboxyl group at the 6-O position of at least one glucose unit of the cyclodextrin ring.

The cyclodextrin ring in the branched cyclodextrin-carboxylic acid has, for example, 6, 7 or 8 glucose units. Preferably, the cyclodextrin ring has 7 glucose units. Examples of the cyclodextrin ring include α-cyclodextrin, β-cyclodextrin and γ-cyclodextrin and the like.

It is preferred that the above-mentioned organic group containing at least one carboxyl group has 1 to 3 glucose units, and that at least one of the hydroxymethyl groups of the glucose units in the organic group is oxidized to a carboxyl group.

Examples of the above-mentioned branched cyclodextrin-carboxylic acid include 6-O-cyclomaltohexaosyl-(6→1)-α-D-glucosyl-(4→1)-O-α-D-glucuronic acid (cyclomaltohexaosyl-(6→1)-α-D-glucopyranosyl-(4→1)-O-α-D-glucopiranosiduronic acid) (hereinafter also abbreviated as α-CyD-$G_2$-COOH; the abbreviations of the following compounds are likewise shown in the parentheses), 6-O-cyclomaltoheptaosyl-(6→1)-α-D-glucosyl-(4→1)-O-α-D-glucuronic acid (cyclomaltoheptaosyl-(6→1)-O-α-D-glucopyranosyl-(4→1)-O-α-D-glucopiranosiduronic acid) (β-CyD-$G_2$-COOH), 6-O-cyclomaltooctaosyl-(6→1)-α-D-glucosyl-(4→1)-O-α-D-glucuronic acid (cyclomaltooctaosyl-(6→1)-O-α-D-glucopyranosyl-(4→1)-O-α-D-glucopiranosiduronic acid) (γ-CyD-$G_2$-COOH), 6-O-cyclomaltohexaosyl-(6→1)-α-D-glucuronic acid (cyclomaltohexaosyl-(6→1)-O-α-D-glucopiranosiduronic acid) (α-CyD-$G_1$-COOH), 6-O-cyclomaltoheptaosyl-(6→1)-α-D-glucuronic acid (cyclomaltoheptaosyl-(6→1)-O-α-D-glucopiranosiduronic acid) (β-CyD-$G_1$-COOH), 6-O-cyclomaltooctaosyl-(6→1)-α-D-glucuronic acid (cyclomaltooctaosyl-(6→1)-O-α-D-glucopiranosiduronic acid) (γ-CyD-$G_1$-COOH), 2-O-(6-cyclomaltohexaosyl)-acetic acid (α-CyD-$CH_2$COOH), 2-O-(6-cyclomaltoheptaosyl)-acetic acid (β-CyD-$CH_2$COOH), 2-O-(6-cyclomaltooctaosyl)-acetic acid (γ-CyD-$CH_2$COOH), 3-O-(6-cyclomaltoheptaosyl)-propionic acid (β-CyD-$CH_2CH_2$COOH), 2-hydroxy-3-O-(6-cyclomaltoheptaosyl)-propionic acid (3-O-(6-cyclomaltoheptaosyl)-2-hydroxy-propionic acid) (β-CyD-$CH_2$CH(OH)—COOH), $7^A$, $7^C$-di-O-[α-D-glucuronyl-(1→4)—O-α-D-glucosyl]-(1→6)-maltoheptaose (β-CyD-$(G_2COOH)_2$), 6-O-cyclomaltoheptaosyl-O-α-D-maltosyl-(4→1)-O-α-D-glucuronic acid (cyclomaltoheptaosyl-(6→1)-O-α-D-glucopyranosyl-(4→1)-O-α-D-glucopyranosyl-(4→1)-O-α-D-glucopiranosiduronic acid) (β-CyD-$G_3$-COOH), and their salts described above [e.g., sodium salt of β-CyD-$G_2$-COOH (sodium cyclomaltoheptaosyl-(6→1)-O-α-D-glucopyranosyl-(4→1)-O-α-D-glucopiranosiduronate (likewise abbreviated as β-CyD-$G_2$-COONa))]. Of these, β-CyD-$G_2$-COONa is preferable.

Specifically, 6-O-cyclomaltohexaosyl-(6→1)-α-D-glucosyl-(4→1)-O-α-D-glucuronic acid (α-CyD-$G_2$-COOH), 6-O-cyclomaltoheptaosyl-(6→1)-α-D-glucosyl-(4→1)-O-α-D-glucuronic acid (β-CyD-$G_2$-COOH) and 6-O-cyclomaltooctaosyl-α-D-glucosyl-(4→1)-O-α-D-glucuronic acid (γ-CyD-$G_2$-COOH) are branched cyclodextrin-carboxylic acids containing, α-cyclodextrin (containing 6 glucose units), β-cyclodextrin (containing 7 glucose units) and γ-cyclodextrin (containing 8 glucose units), respectively. In each of these branched cyclodextrin-carboxylic acids, maltose is attached to one of the glucose units of the cyclodextrin ring through an α-(1→6) linkage, and the hydroxymethyl group at the 6-position of the terminal glucose of the maltose is oxidized to a carboxyl group to form glucuronic acid.

Moreover, 6-O-cyclomaltohexaosyl-(6→1)-α-D-glucuronic acid (α-CyD-$G_1$-COOH), 6-O-cyclomaltoheptaosyl-(6→1)-α-D-glucuronic acid (β-CyD-$G_1$-COOH) and 6-O-cyclomaltooctaosyl-(6→1)-α-D-glucuronic acid (γ-CyD-$G_1$-COOH) are branched cyclodextrin-carboxylic acids wherein glucose is attached to one of the glucose units of the cyclodextrin ring through an α-(1→6) linkage, and the hydroxymethyl group at the 6-position of the branch glucose is oxidized to a carboxyl group to form glucuronic acid.

Further, 2-O-(6-cyclomaltohexaosyl)-acetic acid (α-CyD-$CH_2$COOH), 2-O-(6-cyclomaltoheptaosyl)-acetic acid (α-CyD-$CH_2$COOH) and 2-O-(6-cyclomaltooctaosyl)-acetic acid (γ-CyD-$CH_2$COOH) are branched cyclodextrin-carboxylic acids wherein a carboxymethyl group is attached as a branch to one of the glucose units of the cyclodextrin ring.

These branched cyclodextrin-carboxylic acids or salts thereof are described in JP-A-7-76594 and JP-A-7-215895, and can be produced, for example, a method described in this publication, JP-A-10-210996, JP-A-10-210996 and the like or a method analogous thereto.

These cyclodextrin derivatives readily soluble in water may be used alone or used in combination with two or more kinds thereof.

The amount of the cyclodextrin derivative readily soluble in water to be used is not particularly limited and may be determined from a wide range. In consideration of the water solubility of these substances, a cyclodextrin derivative readily soluble in water is mixed in the range of about 0.1-about 100 mol, preferably about 0.2-about 20 mol, further preferably about 0.5-about 10 mol, more preferably about 1-about 5 mol, relative to 1 mol of compound (I).

The compound (I) and the cyclodextrin derivative represented by the formula (II) (hereinafter to be abbreviated as compound (II)) may form a complex, and as the form of the complex, the coexistent water is preferably evaporated to give a powder, because drugs are generally stable in a solid state. As the evaporation method, lyophilization, vacuum drying and evaporation under atmospheric pressure can be mentioned. For the stability of drug, freeze-drying including drying after freezing and freeze vacuum drying are appropriate.

The production method of this complex includes, for example, the following. That is, compound (II) and compound (I) are prepared into an aqueous solution with water or a buffer generally at near −5° C. to 35° C. This aqueous solution can be obtained by, for example, mixing an aqueous or buffer solution of compound (II) with compound (I), mixing an aqueous or buffer solution of compound (II) with an aqueous or buffer suspension of compound (I), mixing compound (II), compound (I) and water or buffer, or mixing compound (II) with an aqueous or buffer suspension of compound (I). Where necessary, an aqueous solution may be cooled or warmed. The concentration of compound (II) is generally preferably not less than about 50 mg/ml, more preferably not less than about 100 mg/ml. The compound (II) is preferably added in a proportion of about 0.1-about 100-fold mol, preferably about 0.2-about 20-fold mol, further preferably about 0.5-about 10-fold mol, more preferably about 1-about 5-fold mol, relative to compound (I).

After mixing compound (II) and compound (I), a suspension of the mixture is stirred to gradually dissolve compound (I). When dissolution is completed by stirring for generally 1 minute or longer, the stirring is stopped. When the solution contains undissolved portion, it is filtrated to give a complex containing compound (I) having improved solubility.

This complex is powdered by subjecting the obtained solution to freeze-drying, vacuum drying or drying under atmospheric pressure.

After mixing compound (II) and compound (I), a base may be added on demand to the obtained suspension or solution for stabilization. Examples of the base include inorganic bases such as alkali metal hydroxides (e.g., potassium hydroxide, sodium hydroxide and the like), alkali metal hydrogencarbonates (e.g., sodium hydrogencarbonate, potassium hydrogencarbonate and the like), alkali metal carbonates (e.g., sodium carbonate, potassium carbonate), alkali metal phosphates (e.g., sodium phosphate, disodium hydrogenphosphate, potassium phosphate, dipotassium hydrogenphosphate and the like) and the like, and organic bases such as organic monocarboxylic acid alkali metal salt (e.g., sodium acetate, potassium acetate and the like) and the like. The amount of these bases to be added is preferably about 0.0002 to about 0.2 mol, particularly preferably about 0.001 to about 0.035 mol, per 1 mol of compound (I). The base may be added as it is or as an aqueous solution at a suitable concentration.

The powder obtained by these processes is an inclusion compound or a complex formed by electrostatic or hydrophobic interactions or hydrogen bonds, and the like. The powder may contain compound (I) or(and) compound (II) other than an inclusion compound or a complex, such powder is also a complex.

An inclusion compound of compound (I) and a cyclodextrin derivative readily soluble in water can be prepared generally by the following four methods.

(1) Co-precipitation method (Crassons, et al., 5th Int. Conf. Pharmaceutical Technology, Paris, May 30 to Jun. 1, 1989), (2) Lyophilizing or spray drying method (Kurozumi et al., Chem. Pharm. Bull., 23, 3062 (1975); Kata et al., Pharmazie 39, 856 (1984)), (3) Phase-solubility curve crystallization method (Uekama et al., Int. J. Pharmc. 10, 1 (1982)), (4) Milling method (J. Szejtli et al., "Cyclodextrins and their inclusion complexes", Akadeimial Kiado, Budapest (1982), p. 109-114; Kyowa Jap. Prov. Pat. Pubin. No. 106 698 (1982)).

Specifically, the inclusion compound can be prepared as follows:

(1) A compound to be included in the inclusion compound is added to an aqueous solution of the cyclodextrin derivative readily soluble in water. The mixture is stirred (shaken), if necessary, under warming. The remaining unreacted compound to be included is removed by filtration, centrifugation, etc., to obtain an inclusion compound.

(2) The cyclodextrin derivative readily soluble in water is dissolved in water, and a compound to be included is added thereto. While the mixing time is not particularly limited, the two are mixed for, for example, 10 min to several hr, followed by lyophilization (M. Kurozumi et al., Chem. Pharm. Bull., 23, 142 (1975)) to give powder. This powder is dissolved in water, and the unreacted compound to be included is removed to obtain an aqueous solution of an inclusion compound.

(3) A compound to be included is dissolved in an appropriate water-soluble organic solvent in advance. This solution is contacted with cyclodextrin derivative readily soluble in water in an aqueous solution. Then the organic solvent and water are evaporated in vacuo or lyophilized (EP-A-519428, JP-A-5-178765), and water is then added to the residue to dissolve it, and the unreacted compound to be included is removed to obtain an aqueous solution of an inclusion compound.

(4) When an acidic compound is included in the inclusion compound, it is dissolved in ammonia water and cyclodextrin derivative readily soluble in water is added thereto, and the mixture is lyophilized. During the lyophilization, excess ammonia is removed and an inclusion compound is obtained as an ammonium salt of the acidic compound.

(5) A compound to be included is dissolved in a lipophilic organic solvent (e.g., ethyl ether, etc.), and the solution is mixed with a saturated aqueous solution of the cyclodextrin derivative readily soluble in water. While the shaking time is not particularly limited, the mixture is shaken vigorously for, for example, 10 min to several hr and then allowed to stand in a cold place overnight to precipitate an inclusion compound. The precipitate is separated by centrifugation or filtration. The resulting powder is dissolved in water to give an aqueous solution of an inclusion compound.

(6) A powdered compound to be included and powdered cyclodextrin derivative readily soluble in water are mixed, and a small amount of water is added thereto. The mixture is kneaded (Y. Nakai et al., Chem. Pharm. Bull., 26, 2419 (1978)) and then, if necessary, lyophilized.

(7) An aqueous solution of the cyclodextrin derivative readily soluble in water and an aqueous solution of a compound to be included are mixed to give an aqueous solution of an inclusion compound.

The aqueous solution or powder obtained according to a known inclusion method is in most cases an inclusion compound or a complex formed by electrostatic or hydrophobic interactions or hydrogen bonds, etc. Therefore, the term "inclusion compound" used in the present specification means not only an inclusion compound or a complex per se but also a mixture of an inclusion compound, a complex, a free compound to be included and/or a free cyclodextrin derivative readily soluble in water. That is, the powder and aqueous solution obtained may contain, other than an inclusion compound or a complex, a water-insoluble or slightly water soluble compound that is not included or complexed, and/or free branched cyclodextrin. The inclusion compound per se and powder and an aqueous solution like this have extremely high water-solublities and dissolve in water instantly.

The pharmaceutical composition of the present invention may be the aqueous solution per se thus obtained, or a solution obtained by dissolving the resulting powder in a suitable solvent, or, if necessary, a pharmacologically acceptable carrier may be further added as appropriate.

As described above, the pharmaceutical composition of the present invention, particularly the composition for injection, has improved water-solubility, solubility or (and) stability of compound (I) and is free of pyrogen. Therefore, it is highly safe for human and can be used to mammals (e.g., rat, mouse, guinea pig, monkey, bovine, dog, pig, human and the like) as a pharmaceutical agent (e.g., agent for prophylaxis or therapy of various diseases), veterinary drugs and the like. The composition for injection of the present invention can be administered intravenously, intramuscularly, subcutaneously, into the organs or directly into the lesion.

Since compound (I) has low toxicity, an nitric oxide (NO) production-inhibitory effect and an inhibitory effect on the production of an inflammatory cytokine such as TNF-α, IL-1, IL-6, etc., the composition of the present invention, which contains the inventive Compound, a salt thereof or a prodrug thereof is useful as a therapeutic and/or prophylactic agent in a mammal (e.g., cat, cattle, dog, horse, goat, monkey, human and the like) against diseases such as cardiac disease, autoimmune disease, inflammatory disease, central nervous system disease, infectious disease, sepsis, septic shock and the like, including, for example, ichorrhemia, endotoxin shock, exotoxin shock, cardiac deficiency, shock, hypotension, rheumatoid arthritis, osteoarthritis, gastritis, ulcerative colitis, peptic ulcer, stress-induced gastric ulcer, Crohn's disease, autoimmune disease, post-transplant tissue failure and rejection, postischemic re-perfusion failure, acute coronary microvascular embolism, shock-induced vascular embolism (disseminated intravascular coagulation (DIC) and the like), ischemic cerebral disorder, arterial sclerosis, pernicious anemia, Fanconi's anemia, drepanocythemia, pancreatitis, nephrose syndrome, nephritis, renal failure, insulin-dependent diabetes, insulin-independent diabetes, hepatic porphyria, alcoholism, Parkinson's disease, chronic leukemia, acute leukemia, tumor, myeloma, alleviation of side effects caused by anticancer agents, infantile and adult respiratory distress syndrome, pulmonary emphysema, dementia, Alzheimer's disease, multiple sclerosis, vitamin E deficiency, aging, sunburn, muscular dystrophy, myocarditis, cardiomyopathy, myocardial infarction, myocardial post infarction syndrome, osteoporosis, pneumonia, hepatitis, psoriasis, pain, cataract, influenza infection, malaria, human immunodeficiency virus (HIV) infection, radiation hazard, burn, in vitro fertilization efficiency, hypercalcemia, tonic spondylitis, osteopenia, bone Paget's disease, osteomalacia, fracture, acute bacterial meningitis, *Helicobacter pylori* infection, invasive staphylococcal infection, tuberculosis, systemic mycosis, herpes simplex virus infection, varicella-helpes zoster virus infection, human papilloma virus infection, acute viral encephalitis, encephalitis, asthma, atopic dermatitis, allergic rhinitis, reflux esophargitis, fever, hyper cholesteremia, hyperglycemia, hyperlipidemia, diabetic complication, diabetic renal disease, diabetic neuropathy, diabetic retinopathy, gout, gastric atony, hemorrhoid, systemic lupus erythematosus, spinal damage, insomnia, schizophrenia, epilepsy, cirrhosis, hepatic failure, instable angina, valvular disease, dialysis-induced thrombocytopenia, acute ischemic cerebral apoplexy, acute cerebral thrombosis, cancer metastasis, urinary bladder cancer, mammary cancer, uterine cervical cancer, colon cancer, gastric cancer, ovarian cancer, prostatic cancer, parvicellular pulmonary cancer, non-parvicellular pulmonary cancer, malignant melanoma, Hodgkin's disease, non-Hodgkin lymphoma and the like.

While the dose of the composition of the present invention may vary depending on the kind of the inventive Compound, age, body weight and condition, the dosage form, the mode and the period of the treatment, etc., it may, for example, be generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg, as the inventive Compound (I), per day in a patient having a sepsis (adult weighing about 60 kg), said daily dose being given intravenously all at once or in several portions during a day. It is a matter of course that a lower daily dose may be sufficient or an excessive dose may be required since the dose may vary depending on various factors as discussed above.

In the present invention, the "effective amount" means an effective amount of compound (I) and "administration of an effective amount" means administering the pharmaceutical composition of the present invention containing an effective amount of compound (I).

EXAMPLES

The present invention is explained in detail in the following by referring to Reference Examples, Examples, Comparative Examples and Experimental Examples, which are not to be construed as limitative.

The proportion of the mixed solvent is a weight mixing ratio of each solvent, wherein % means % by weight unless otherwise specified.

A high polarity diastereomer means a diastereomer having a smaller Rf value when determined by normal phase thin layer chromatography under the same conditions (e.g., use of ethyl acetate/hexane as a solvent), and a low polarity diastereomer means a diastereomer having a larger Rf value.

The following Reference Examples A can be produced according to Reference Examples of WO99/46424 and Reference Example B can be produced according to Examples of WO99/46424.

[Reference Examples A]

Reference Example A1 ethyl 2-sulfo-1-cyclohexene-1-carboxylate
Reference Example A2 ethyl 2-chlorosulfonyl-1-cyclohexene-1-carboxylate
Reference Example A3 ethyl 2-chlorosulfonyl-1-cyclopentene-1-carboxylate
Reference Example A4 ethyl 2-chlorosulfonyl-1-cycloheptene-1-carboxylate
Reference Example A5 sodium 6-[N-(4-chloro-2-fluorophenyl)-sulfamoyl]-1-cyclohexene-1-carboxylate
Reference Example A6 1-(3-fluoro-4-nitrophenyl)-1H-1,2,4-triazole
Reference Example A7 1-(4-amino-3-fluorophenyl)-1H-1,2,4-triazole
Reference Example A8 methyl 4-benzyloxycarbonylamino-3-chlorobenzoate
Reference Example A9 4-benzyloxycarbonylamino-3-chlorobenzoic acid
Reference Example A10 tert-butyl N-(4-benzyloxycarbonylamino-3-chlorobenzoyl)glycinate
Reference Example A11 tert-butyl N-(4-amino-3-chlorobenzoyl)-glycinate
Reference Example A12 6-[N-(2,4-difluorophenyl)sulfamoyl]-1-cyclohexene-1-carboxylic acid
Reference Example A13 ethyl 2-mercapto-5-phenyl-1-cyclohexene-1-carboxylate
Reference Example A14 ethyl 2-chlorosulfonyl-5-phenyl-1-cyclohexene-1-carboxylate
Reference Example A15 ethyl 5-tert-butyl-2-mercapto-1-cyclohexene-1-carboxylate
Reference Example A16 ethyl 5-tert-butyl-2-chlorosulfonyl-1-cyclohexene-1-carboxylate
Reference Example A17 ethyl 5,5-dimethyl-2-mercapto-1-cyclohexene-1-carboxylate
Reference Example A18 ethyl 2-chlorosulfonyl-5,5-dimethyl-1-cyclohexene-1-carboxylate

[Reference Examples B]

Reference Example B1 ethyl 6-[N-(4-chloro-2-fluorophenyl)-sulfamoyl]-1-cyclohexene-1-carboxylate (compound 1)
Reference Example B2 ethyl 6-[N-(4-chloro-2-fluorophenyl)-N-methylsulfamoyl]-1-cyclohexene-1-carboxylate (compound 2)
Reference Example B3 ethyl 6-[N-(2,4-difluorophenyl)sulfamoyl]-1-cyclohexene-1-carboxylate (compound 3)
Reference Example B4 ethyl 6-[N-(2,6-diisopropylphenyl)-sulfamoyl]-1-cyclohexene-1-carboxylate (compound 4)
Reference Example B5 ethyl 6-[N-(4-nitrophenyl)sulfamoyl]-1-cyclohexene-1-carboxylate (compound 5)
Reference Example B6 ethyl 6-(N-phenylsulfamoyl)-1-cyclohexene-1-carboxylate (compound 6) ethyl 2-(N-phenylsulfamoyl)-1-cyclohexene-1-carboxylate (compound 7)
Reference Example B7 ethyl 2-[N-(4-chloro-2-fluorophenyl)-sulfamoyl]-1-cyclohexene-1-carboxylate (compound 9)
Reference Example B8 2-(4-methoxyphenyl)-4,5,6,7-tetrahydro-1,2-benzisothiazol-3 (2H)-one 1,1-dioxide (compound 67) ethyl 2-[N-(4-methoxyphenyl)sulfamoyl]-1-cyclohexene-1-carboxylate (compound 8)
Reference Example B9 ethyl 6-[N-(2-fluorophenyl)sulfamoyl]-1-cyclohexene-1-carboxylate (compound 10)
Reference Example B10 ethyl 6-[N-(3-fluorophenyl)sulfamoyl]-1-cyclohexene-1-carboxylate (compound 11)
Reference Example B11 2-(4-fluorophenyl)-4,5,6,7-tetrahydro-1,2-benzisothiazol-3 (2H)-one 1,1-dioxide (compound 68) ethyl 6-[N-(4-fluorophenyl)sulfamoyl]-1-cyclohexene-1-carboxylate (compound 12) ethyl 2-[N-(4-fluorophenyl)sulfamoyl]-1-cyclohexene-1-carboxylate (compound 18)
Reference Example B12 ethyl 6-[N-(2,6-difluorophenyl)-sulfamoyl]-1-cyclohexene-1-carboxylate (compound 13)
Reference Example B13 ethyl 6-[N-(2,3-difluorophenyl)-sulfamoyl]-1-cyclohexene-1-carboxylate (compound 14)
Reference Example B14 ethyl 6-[N-(2,5-difluorophenyl)-sulfamoyl]-1-cyclohexene-1-carboxylate (compound 15)
Reference Example B15 ethyl 6-[N-(3,4-difluorophenyl)-sulfamoyl]-1-cyclohexene-1-carboxylate (compound 16)
Reference Example B16 ethyl 6-[N-(3,5-difluorophenyl)-sulfamoyl]-1-cyclohexene-1-carboxylate (compound 17)
Reference Example B17 1-ethyl 6-[N-(2,4-difluorophenyl)-sulfamoyl]-1-cyclohexene-1-carboxylate (compound 19) d-ethyl 6-[N-(2,4-difluorophenyl)sulfamoyl]-1-cyclohexene-1-carboxylate (compound 20)
Reference Example B18 ethyl 6-[N-(2-ethoxycarbonylphenyl)-sulfamoyl]-1-cyclohexene-1-carboxylate (compound 21)
Reference Example B19 methyl 6-[N-(2,4-difluorophenyl)-sulfamoyl]-1-cyclohexene-1-carboxylate (compound 22)
Reference Example B20 propyl 6-[N-(2,4-difluorophenyl)-sulfamoyl]-1-cyclohexene-1-carboxylate (compound 23)
Reference Example B21 methyl 6-[N-(4-chloro-2-fluorophenyl)-sulfamoyl]-1-cyclohexene-1-carboxylate (compound 24)
Reference Example B22 isopropyl 6-[N-(2,4-difluorophenyl)-sulfamoyl]-1-cyclohexene-1-carboxylate (compound 25)
Reference Example B23 ethyl 6-[N-(2-methoxycarbonylphenyl)-sulfamoyl]-1-cyclohexene-1-carboxylate (compound 26)
Reference Example B24 ethyl 6-[N-(2-fluoro-4-methylphenyl)-68 sulfamoyl]-1-cyclohexene-1-carboxylate (compound 27)
Reference Example B25 ethyl 6-[N-(2-chlorophenyl)sulfamoyl]-1-cyclohexene-1-carboxylate (compound 28)
Reference Example B26 ethyl 6-[N-(2-chloro-4-fluorophenyl)-sulfamoyl]-1-cyclohexene-1-carboxylate (compound 29)
Reference Example B27 ethyl 6-[N-(4-chlorophenyl)sulfamoyl]-1-cyclohexene-1-carboxylate (compound 30)
Reference Example B28 ethyl 6-[N-(2,3,4-trifluorophenyl)-sulfamoyl]-1-cyclohexene-1-carboxylate (compound 31)
Reference Example B29 isobutyl 6-[N-(2,4-difluorophenyl)-sulfamoyl]-1-cyclohexene-1-carboxylate (compound 32)
Reference Example B30 butyl 6-[N-(2,4-difluorophenyl)-sulfamoyl]-1-cyclohexene-1-carboxylate (compound 33)
Reference Example B31 ethyl 6-[N-(4-bromo-2-fluorophenyl)-sulfamoyl]-1-cyclohexene-1-carboxylate (compound 34)
Reference Example B32 ethyl 6-[N-(2,4-dichlorophenyl)-sulfamoyl]-1-cyclohexene-1-carboxylate (compound 35)
Reference Example B33 ethyl 6-[N-(2-acetoxyphenyl)sulfamoyl]-1-cyclohexene-1-carboxylate (compound 36)
Reference Example B34 ethyl 6-[N-(3-chlorophenyl)sulfamoyl]-1-cyclohexene-1-carboxylate (compound 37)
Reference Example B35 ethyl 6-[N-(2,3-dichlorophenyl)-sulfamoyl]-1-cyclohexene-1-carboxylate (compound 38)

Reference Example B36 ethyl 6-[N-(2-ethylphenyl)sulfamoyl]-1-cyclohexene-1-carboxylate (compound 39)

Reference Example B37 ethyl 6-[N-[4-(2H-1,2,3-triazol-2-yl)phenyl]sulfamoyl]-1-cyclohexene-1-carboxylate (compound 40)

Reference Example B38 ethyl 6-[N-(2,5-dichlorophenyl)-sulfamoyl]-1-cyclohexene-1-carboxylate (compound 41)

Reference Example B39 ethyl 6-[N-(2-trifluoromethoxyphenyl)-sulfamoyl]-1-cyclohexene-1-carboxylate (compound 42)

Reference Example B40 ethyl 6-[N-(2,4,5-trifluorophenyl)-sulfamoyl]-1-cyclohexene-1-carboxylate (compound 43)

Reference Example B41 ethyl 6-[N-[4-(2H-tetrazol-2-yl)phenyl]sulfamoyl]-1-cyclohexene-1-carboxylate (compound 44)

Reference Example B42 ethyl 6-[N-(2-chloro-4-methylphenyl)-sulfamoyl]-1-cyclohexene-1-carboxylate (compound 45)

Reference Example B43 ethyl 6-[N-(4-fluoro-2-methylphenyl)-sulfamoyl]-1-cyclohexene-1-carboxylate (compound 46)

Reference Example B44 ethyl 6-[N-(2,6-dichlorophenyl)-sulfamoyl]-1-cyclohexene-1-carboxylate (compound 47)

Reference Example B45 ethyl 6-[N-[4-(1H-tetrazol-1-yl)phenyl)sulfamoyl]-1-cyclohexene-1-carboxylate (compound 48)

Reference Example B46 ethyl 6-[N-(4-(1H-1,2,3-triazol-1-yl)phenyl]sulfamoyl]-1-cyclohexene-1-carboxylate (compound 49)

Reference Example B47 ethyl 6-[N-(2-trifluoromethylphenyl)-sulfamoyl]-1-cyclohexene-1-carboxylate (compound 50)

Reference Example B48 ethyl 6-[N-(4-methoxycarbonylphenyl)-sulfamoyl]-1-cyclohexene-1-carboxylate (compound 51)

Reference Example B49 benzyl 6-[N-(2,4-difluorophenyl)-sulfamoyl]-1-cyclohexene-1-carboxylate (compound 52)

Reference Example B50 ethyl 6-[N-[4-[2,3-bis(tert-butoxycarbonyl)guanidinomethyl]phenyl]sulfamoyl]-1-cyclohexene-1-carboxylate (compound 53)

Reference Example B51 ethyl 6-[N-(2-chloro-4-methoxycarbonylphenyl)sulfamoyl]-1-cyclohexene-1-carboxylate (compound 54)

Reference Example B52 and ethyl 6-[N-(2-chloro-4-cyanophenyl)-sulfamoyl]-1-cyclohexene-1-carboxylate (compound 55)

Reference Example B53 2-hydroxyethyl 6-[N-(2,4-difluorophenyl)-sulfamoyl]-1-cyclohexene-1-carboxylate (compound 56)

Reference Example B54 ethyl 6-[N-[2-fluoro-4-(1H-1,2,4-triazol-1-yl)phenyl]sulfamoyl]-1-cyclohexene-1-carboxylate (compound 57)

Reference Example B55 ethyl 2-[N-(2,4-difluorophenyl)-sulfamoyl]-1-cyclopentene-1-carboxylate (compound 66) ethyl 5-[N-(2,4-difluorophenyl)sulfamoyl]-1-cyclopentene-1-carboxylate (compound 58)

Reference Example B56 tert-butyl [6-[N-(2,4-difluorophenyl)-sulfamoyl]-1-cyclohexen-1-yl]carbonyloxyacetate (compound 59)

Reference Example B57 [6-[N-(2,4-difluorophenyl)sulfamoyl]-1-cyclohexen-1-yl]carbonyloxyacetic acid (compound 60)

Reference Example B58 ethyl 7-[N-(2,4-difluorophenyl)-sulfamoyl]-1-cycloheptene-1-carboxylate (compound 61)

Reference Example B59 ethyl 6-[N-[2-chloro-4-(N-tert-butoxycarbonylmethylcarbamoyl)phenyl]sulfamoyl]-1-cyclohexene-1-carboxylate (compound 62)

Reference Example B60 ethyl 6-[N-[2-chloro-4-(N-ethoxycarbonylmethylcarbamoyl)phenyl]sulfamoyl]-1-cyclohexene-1-carboxylate (compound 63)

Reference Example B61 ethyl 5-[N-(2-chloro-4-fluorophenyl)-sulfamoyl]-1-cyclopentene-1-carboxylate (compound 64)

Reference Example B62 2-[4-(2,2,3,3,3-pentafluoropropoxy)-phenyl]-4,5,6,7-tetrahydro-1,2-benzisothiazol-3(2H)-one 1,1-dioxide (compound 69)

Reference Example B63 ethyl 7-[N-(2-chloro-4-fluorophenyl)-sulfamoyl]-1-cycloheptene-1-carboxylate (compound 65)

Reference Example B64 2-(2,4-difluorophenyl)-5,6,7,7a-tetrahydro-1,2-benzisothiazol-3 (2H)-one 1,1-dioxide (compound 70)

Reference Example B65 ethyl 6-[N-(2-chloro-4-fluorophenyl)-sulfamoyl]-1-cyclohexene-1-carboxylate (compound 29)

Reference Example B66 1-ethyl 6-[N-(2-chloro-4-fluorophenyl)-sulfamoyl]-1-cyclohexene-1-carboxylate (compound 71) d-ethyl 6-[N-(2-chloro-4-fluorophenyl)sulfamoyl]-1-cyclohexene-1-carboxylate (compound 72)

Reference Example B67 ethyl 6-[N-(2-bromo-4-fluorophenyl)-sulfamoyl]-1-cyclohexene-1-carboxylate (compound 73)

Reference Example B68 ethyl 6-[N-(4-bromo-2-chlorophenyl)-sulfamoyl]-1-cyclohexene-1-carboxylate (compound 74)

Reference Example B69 high polarity diastereomer (compound 75) and low polarity diastereomer (compound 76) of ethyl 6-[N-(2,4-difluorophenyl)sulfamoyl]-3-phenyl-1-cyclohexene-1-carboxylate Reference Example B70 high polarity diastereomer (compound 77) and low polarity diastereomer (compound 78) of ethyl 6-[N-(2-chloro-4-fluorophenyl)sulfamoyl]-3-phenyl-1-cyclohexene-1-carboxylate Reference Example B71 high polarity diastereomer (compound 79) and low polarity diastereomer (compound 80) of ethyl 6-[N-(2,4-difluorophenyl)sulfamoyl]-3-tert-butyl-1-cyclohexene-1-carboxylate Reference Example B72 high polarity diastereomer (compound 81) and low polarity diastereomer (compound 82) of ethyl 6-[N-(2-chloro-4-fluorophenyl)sulfamoyl]-3-tert-butyl-1-cyclohexene-1-carboxylate Reference Example B73 ethyl 6-[N-(2,4-difluorophenyl)-sulfamoyl]-3,3-dimethyl-1-cyclohexene-1-carboxylate (compound 83)

Reference Example B74 ethyl 6-[N-(2-chloro-4-fluorophenyl)-sulfamoyl]-3,3-dimethyl-1-cyclohexene-1-carboxylate (compound 84)

Reference Example B75 ethyl 3-bromo-6-[N-(2,4-difluorophenyl)-sulfamoyl]-1-cyclohexene-1-carboxylate (compound 85)

Furthermore, specific examples are shown in Tables 1-5.

TABLE 1
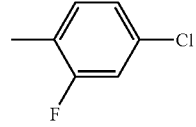
| Compound No. | R¹ | R² | Ar | n |
|---|---|---|---|---|
| 1 | $C_2H_5$ | H | 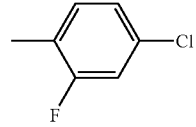 | 2 |
| 2 | $C_2H_5$ | $CH_3$ | 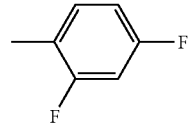 | 2 |
| 3 | $C_2H_5$ | H | 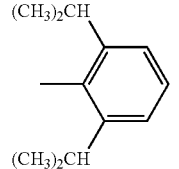 | 2 |
| 4 | $C_2H_5$ | H | 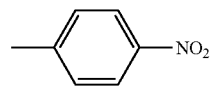 | 2 |
| 5 | $C_2H_5$ | H | 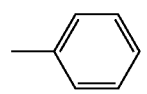 | 2 |
| 6 | $C_2H_5$ | H | 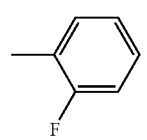 | 2 |
| 10 | $C_2H_5$ | H | 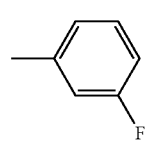 | 2 |
| 11 | $C_2H_5$ | H | 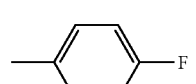 | 2 |
| 12 | $C_2H_5$ | H | 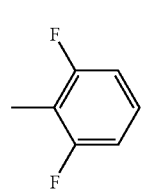 | 2 |
| 13 | $C_2H_5$ | H |  | 2 |

TABLE 1-continued
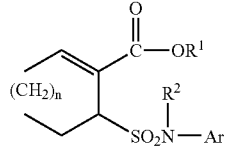
| Compound No. | R¹ | R² | Ar | n |
|---|---|---|---|---|
| 14 | $C_2H_5$ | H | 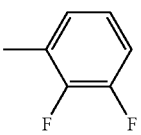 | 2 |
| 15 | $C_2H_5$ | H | 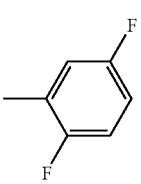 | 2 |
| 16 | $C_2H_5$ | H | 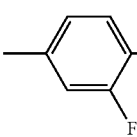 | 2 |
| 17 | $C_2H_5$ | H | 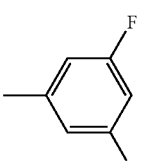 | 2 |
| 19 (1-form) | $C_2H_5$ | H | 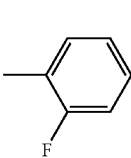 | 2 |
| 20 (d-form) | $C_2H_5$ | H | 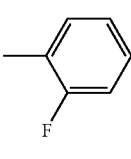 | 2 |
| 21 | $C_2H_5$ | H | 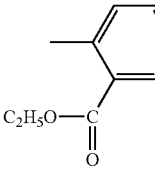 | 2 |
| 22 | $CH_3$ | H | 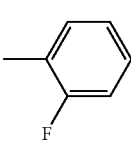 | 2 |

TABLE 1-continued
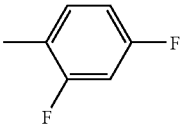
| Compound No. | R¹ | R² | Ar | n |
|---|---|---|---|---|
| 23 | (CH₂)₂CH₃ | H | 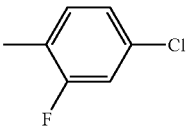 | 2 |
| 24 | CH₃ | H | 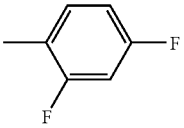 | 2 |
| 25 | CH(CH₃)₂ | H | 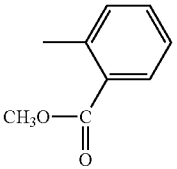 | 2 |
| 26 | C₂H₅ | H | 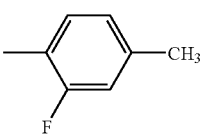 | 2 |
| 27 | C₂H₅ | H | 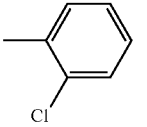 | 2 |
| 28 | C₂H₅ | H | 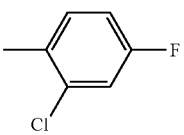 | 2 |
| 29 | C₂H₅ | H |  | 2 |
| 30 | C₂H₅ | H | 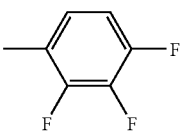 | 2 |
| 31 | C₂H₅ | H | | 2 |

TABLE 1-continued
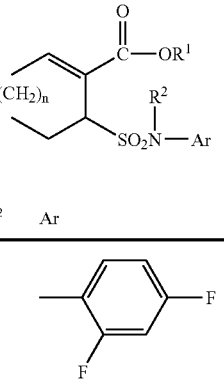
| Compound No. | R¹ | R² | Ar | n |
|---|---|---|---|---|
| 32 | CH$_2$CH(CH$_3$)$_2$ | H | 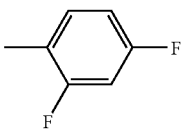 | 2 |
| 33 | (CH$_2$)$_3$CH$_3$ | H | 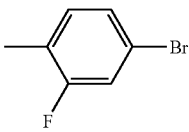 | 2 |
| 34 | C$_2$H$_5$ | H | 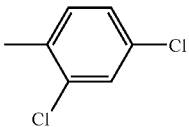 | 2 |
| 35 | C$_2$H$_5$ | H | 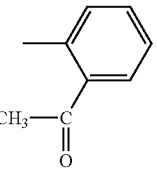 | 2 |
| 36 | C$_2$H$_5$ | H | 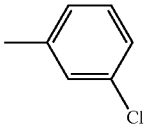 | 2 |
| 37 | C$_2$H$_5$ | H | 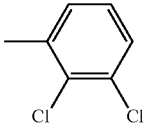 | 2 |
| 38 | C$_2$H$_5$ | H | 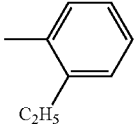 | 2 |
| 39 | C$_2$H$_5$ | H | 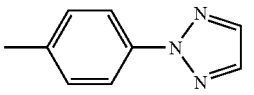 | 2 |
| 40 | C$_2$H$_5$ | H |  | 2 |

TABLE 1-continued
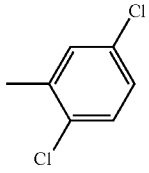
| Compound No. | R¹ | R² | Ar | n |
|---|---|---|---|---|
| 41 | $C_2H_5$ | H | 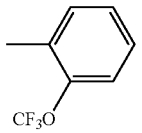 | 2 |
| 42 | $C_2H_5$ | H | 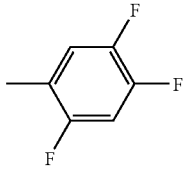 | 2 |
| 43 | $C_2H_5$ | H | 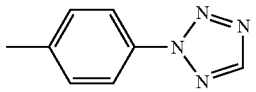 | 2 |
| 44 | $C_2H_5$ | H | 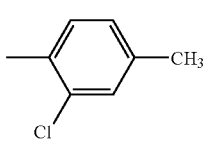 | 2 |
| 45 | $C_2H_5$ | H | 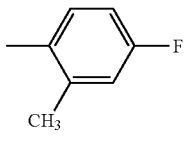 | 2 |
| 46 | $C_2H_5$ | H | 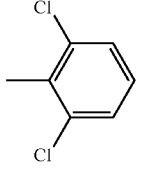 | 2 |
| 47 | $C_2H_5$ | H | 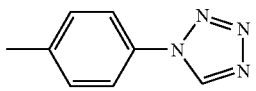 | 2 |
| 48 | $C_2H_5$ | H | 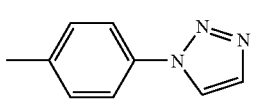 | 2 |
| 49 | $C_2H_5$ | H |  | 2 |

TABLE 1-continued
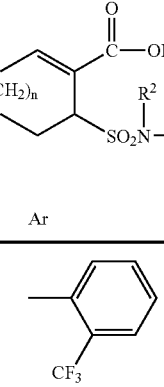
| Compound No. | R¹ | R² | Ar | n |
|---|---|---|---|---|
| 50 | C₂H₅ | H | 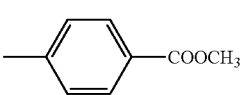 | 2 |
| 51 | C₂H₅ | H | 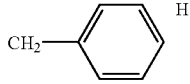 | 2 |
| 52 | 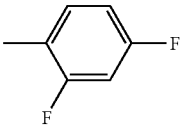 | H | 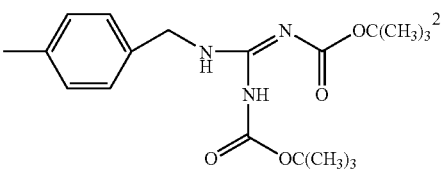 | 2 |
| 53 | C₂H₅ | H | 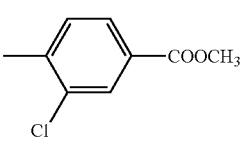 | 2 |
| 54 | C₂H₅ | H | 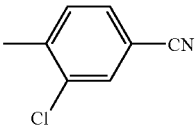 | 2 |
| 55 | C₂H₅ | H | 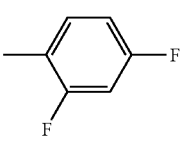 | 2 |
| 56 | (CH₂)₂OH | H | 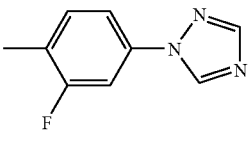 | 2 |
| 57 | C₂H₅ | H | 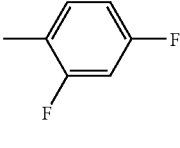 | 2 |
| 58 | C₂H₅ | H |  | 1 |

TABLE 1-continued
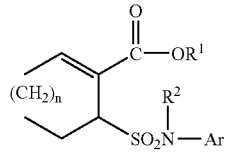
| Compound No. | R¹ | R² | Ar | n |
|---|---|---|---|---|
| 59 | $CH_2COOC(CH_3)_3$ | H | 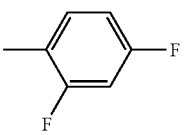 | 2 |
| 60 | $CH_2COOH$ | H | 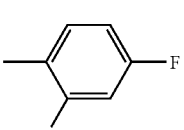 | 2 |
| 61 | $C_2H_5$ | H | 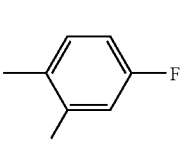 | 3 |
| 62 | $C_2H_5$ | H | 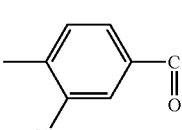 | 2 |
| 63 | $C_2H_5$ | H | 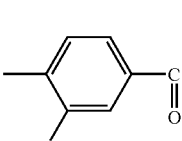 | 2 |
| 64 | $C_2H_5$ | H | 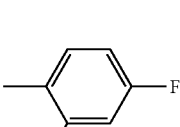 | 1 |
| 65 | $C_2H_5$ | H | 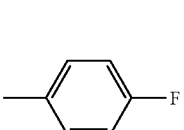 | 3 |
| 71 (1-form) | $C_2H_5$ | H | 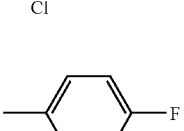 | 2 |

TABLE 1-continued
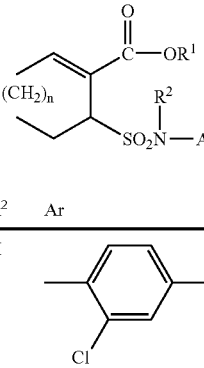
| Compound No. | R¹ | R² | Ar | n |
|---|---|---|---|---|
| 72 (d-form) | $C_2H_5$ | H | 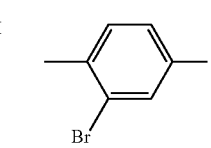 | 2 |
| 73 | $C_2H_5$ | H | 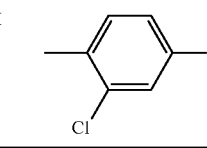 | 2 |
| 74 | $C_2H_5$ | H | 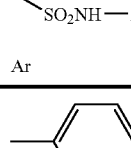 | 2 |
TABLE 2
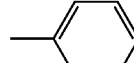
| Compound No. | R¹ | Ar | n |
|---|---|---|---|
| 7 | $C_2H_5$ | 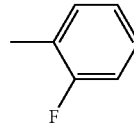 | 2 |
| 8 | $C_2H_5$ | 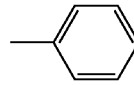 | 2 |
| 9 | $C_2H_5$ | 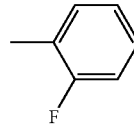 | 2 |
| 18 | $C_2H_5$ | 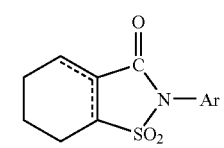 | 2 |
| 66 | $C_2H_5$ | 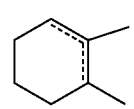 | 1 |
TABLE 3
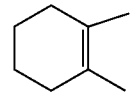
| Compound No. | | Ar |
|---|---|---|
| 67 | 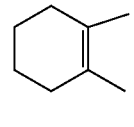 | 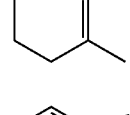 |
| 68 | 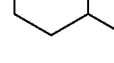 |  |
| 69 | 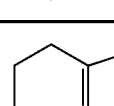 | 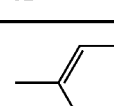 |
| 70 | 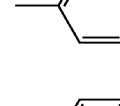 | 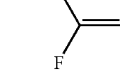 |

TABLE 4

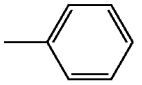

| Compound No. | R¹ | R² | R* | Ar |
|---|---|---|---|---|
| 75 (high polarity diastereomer) | $C_2H_5$ | H | 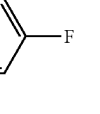 | 2,4-difluorophenyl |
| 76 (low polarity diastereomer) | $C_2H_5$ | H | phenyl | 2,4-difluorophenyl |
| 77 (high polarity diastereomer) | $C_2H_5$ | H | phenyl | 2-chloro-4-fluorophenyl |
| 78 (low polarity diastereomer) | $C_2H_5$ | H | phenyl | 2-chloro-4-fluorophenyl |
| 79 (high polarity diastereomer) | $C_2H_5$ | H | $C(CH_3)_3$ | 2,4-difluorophenyl |
| 80 (low polarity diastereomer) | $C_2H_5$ | H | $C(CH_3)_3$ | 2,4-difluorophenyl |
| 81 (high polarity diastereomer) | $C_2H_5$ | H | $C(CH_3)_3$ | 2-chloro-4-fluorophenyl |
| 82 (low polarity diastereomer) | $C_2H_5$ | H | $C(CH_3)_3$ | 2-chloro-4-fluorophenyl |
| 85 | $C_2H_5$ | H | Br | 2,4-difluorophenyl |

TABLE 5

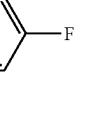

| Compound No. | Ar |
|---|---|
| 83 | 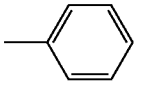 2,4-difluorophenyl |
| 84 | 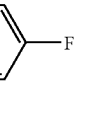 2-chloro-4-fluorophenyl |

Example 1

| 1) compound 72 of Reference Example B66 | 100 mg |
|---|---|
| 2) polyoxyethylene glycerol triricinoleate 35 | 35 mg |
| 3) ethanol | 4 ml |

Polyoxyethylene glycerol triricinoleate 35 (1 ml) and ethanol (4 ml) were added to compound 72 (100 mg) of Reference Example B66 and dissolved.

Example 2

| 1) compound 72 of Reference Example B66 | 100 mg |
|---|---|
| 2) polyoxyethylene glycerol triricinoleate 35 | 3.25 ml |
| 3) ethanol | 1.75 ml |

Polyoxyethylene glycerol triricinoleate 35 (3.25 ml) and ethanol (1.75 ml) were added to compound 72 (100 mg) of Reference Example B66 and dissolved.

Example 3

| 1) compound 72 of Reference Example B66 | 8 mg |
|---|---|
| 2) G2-β-CyD | 145.2 mg |

Distilled water for injection (1 ml) was added to G2-β-CyD (145.2 mg) and dissolved. Thereto was added compound 72 (8 mg) of Reference Example B66 and dissolved.

Example 4

| | |
|---|---|
| 1) compound 72 of Reference Example B66 | 8 mg |
| 2) G2-β-CyD | 145.2 mg |

G2-β-CyD (145.2 mg) was added to phosphate citrate buffer (pH 7) and dissolved. Thereto was added compound 72 (8 mg) of Reference Example B66 and dissolved.

Example 5

| | |
|---|---|
| 1) compound 72 of Reference Example B66 | 5 mg |
| 2) 40% aqueous solution of 2-hydroxypropyl-β-cyclodextrin | 3 ml |

40% Aqueous solution of 2-hydroxypropyl-β-cyclodextrin (3 ml) was added to compound 72 (5 mg) of Reference Example B66 and dissolved.

Example 6

| | |
|---|---|
| 1) compound 72 of Reference Example B66 | 5 mg |
| 2) 40% aqueous solution of 2-hydroxypropyl-β-cyclodextrin | 3 ml |

40% Aqueous solution of 2-hydroxypropyl-β-cyclodextrin (3 ml) was added to compound 72 (5 mg) of Reference Example B66 and dissolved. It is adjusted to pH 7 with phosphate citrate buffer.

Comparative Example 1

Solubilizing Effect of Solubilizer on Compound 72

The solvent (1 ml) shown in Table 6 was added to compound 72 (5 mg), and solubility was confirmed after sonication and vortex mixing. When not dissolved, the solvent (1 ml) was further added, and solubility was confirmed after sonication and vortex mixing in the same manner. The concentration at the time of dissolution was taken as solubility.

The 10% aqueous solution of sodium desoxycholate showed a solubilizing effect as compared to solubility in water, but the solubility of 1 mg/ml expected to achieve for the development of injection was not afforded.

TABLE 6

| Solvent | Solubility |
|---|---|
| water | 0.013 mg/ml |
| 10% sodium desoxycholate | about 0.7 mg/ml |
| 10% Pluronic F68* | Not more than 0.5 mg/ml** |
| 10% nicotinamide | Not more than 0.5 mg/ml** |
| 10% sodium salicylate | Not more than 0.5 mg/ml** |
| 10% ethanol | Not more than 0.5 mg/ml** |

*polyoxyethylene(160)polyoxypropylene(30)glycol
**Concentrations below the indicated concentration were not examined.

Experimental Example 1

Polyoxyethylene glycerol triricinoleate 35/ethanol solution (50 μl) at a ratio (weight ratio) shown in Table 7 was added to compound 72 (5 mg), the mixture was stirred and the solubility was confirmed. The compound 72 dissolved at any mixing ratio, affording a clear solution. Accordingly, the solubility of compound 72 in the solvent used was not less than 100 mg/ml. From Table 7, the solubility of compound 72 was found to have markedly increased in the pharmaceutical composition of the present invention.

TABLE 7

| Formulation | Polyoxyethylene castor oil*/ethanol (w/w) | Solubility |
|---|---|---|
| 1 | 20/80 | Not less than 100 mg/ml |
| 2 | 65/35 | Not less than 100 mg/ml |
| 3 | 100/0 | Not less than 100 mg/ml |

*polyoxyethylene glycerol triricinoleate 35

Experimental Example 2

Drug solutions according to Formulation 1 and Formulation 2 of Experimental Example 1 and having a concentration of compound 72 of 20 mg/ml were prepared, and subjected to a stability test. The results shown in Table 8 were obtained. From Table 8, it was found that the pharmaceutical composition of the present invention was extremely stable.

TABLE 8

| Formulation | Preservation condition | Dissolution state | Residual ratio (%) | pH |
|---|---|---|---|---|
| 1 | initial | pale yellow, clear | 100 | 8.1 |
| | 25° C. × 2 weeks | pale yellow, clear | 103.0 | 8.0 |
| 2 | initial | pale yellow, clear | 100 | 8.2 |
| | 25° C. × 2 weeks | pale yellow, clear | 99.0 | 8.2 |

Experimental Example 3

Compound 72 was dissolved in a solution of polyoxyethylene glycerol triricinoleate 35/ethanol solution (weight ratio 20/80), and maleic acid or anhydrous citric acid was added as a pH adjusting agent in an amount shown in Table 9 to give a drug solution. The prepared drug solution was filtrated through a 0.22 μm filter. The filtrate (1 ml) was filled in an ampoule (1P), and the head space was substituted with nitrogen and the ampoule was sealed.

A stability test was performed to give the results of Table 10. From Table 10, it was found that the pharmaceutical composition of the present invention was extremely stable.

TABLE 9

| Formulation | | Amount added |
|---|---|---|
| 4 | compound 72 | 50 mg |
| | polyoxyethylene castor oil* | 200 mg |
| | ethanol | 800 mg |
| | maleic acid | 0.3 mg |
| 5 | compound 72 | 50 mg |
| | polyoxyethylene castor oil* | 200 mg |
| | ethanol | 800 mg |
| | anhydrous citric acid | 3 mg |

*polyoxyethylene glycerol triricinoleate 35

TABLE 10

| Formulation | Preservation condition | Dissolution state | Residual ratio (%) | pH |
|---|---|---|---|---|
| 4 | initial | pale yellow, clear | 100 | 5.2 |
|   | 60° C. × 1 week | pale yellow, clear | 98.0 | 4.5 |
|   | 60° C. × 2 weeks | pale yellow, clear | 97.5 | 4.7 |
| 5 | initial | pale yellow, clear | 100 | 5.1 |
|   | 60° C. × 1 week | pale yellow, clear | 97.1 | 4.9 |
|   | 60° C. × 2 weeks | pale yellow, clear | 96.7 | 5.0 |

Experimental Example 4

Polyoxyethylene hydrogenated castor oil 50/ethanol solution (50 μl) at a ratio (weight ratio) shown in Table 11 was added to compound 72 (5 mg), the mixture was stirred and the solubility was confirmed. The compound 72 dissolved at any mixing ratio, affording a clear solution. Accordingly, the solubility of compound 72 in the solvent used was not less than 100 mg/ml. From Table 11, the solubility of compound 72 was found to have markedly increased in the pharmaceutical composition of the present invention.

TABLE 11

| Polyoxyethylene hydrogenated castor oil 50/ethanol (w/w) | Solubility |
|---|---|
| 20/80 | Not less than 100 mg/ml |
| 65/35 | Not less than 100 mg/ml |

Experimental Example 5

Compound 72 was dissolved in a solution of polyoxyethylene hydrogenated castor oil 50/ethanol (weight ratio 20/80), and anhydrous citric acid was added as a pH adjusting agent in an amount described in Table 12 to give a drug solution. The prepared drug solution was filtrated through a 0.22 μm filter. The filtrate (1 ml) was filled in an ampoule (1P), and the head space was substituted with nitrogen and the ampoule was sealed.

A stability test was performed to give the results of Table 13. From Table 13, it was found that the pharmaceutical composition of the present invention was extremely stable.

TABLE 12

| Formulation | Formulation | Amount added |
|---|---|---|
| 6 | compound 72 | 50 mg |
|   | polyoxyethylene hydrogenated castor oil 50 | 200 mg |
|   | ethanol | 800 mg |
|   | anhydrous citric acid | 3 mg |

TABLE 13

| Formulation | Preservation condition | Dissolution state | Residual ratio(%) | pH |
|---|---|---|---|---|
| 6 | initial | Colorless, clear | 100 | 4.9 |
|   | 60° C. × 1 week | Colorless, clear | 99.7 | 4.8 |

Experimental Example 6

Polyoxyethylene hydrogenated castor oil 60/ethanol solution (50 μl) at a ratio (weight ratio) shown in Table 14 was added to compound 72 (5 mg), the mixture was stirred and the solubility was confirmed. The compound 72 dissolved to give a clear solution. Accordingly, the solubility of compound 72 in the solvent used was not less than 100 mg/ml. From Table 14, the solubility of compound 72 was found to have markedly increased in the pharmaceutical composition of the present invention.

TABLE 14

| Polyoxyethylene hydrogenated castor oil 60/ethanol (w/w) | Solubility |
|---|---|
| 20/80 | Not less than 100 mg/ml |

Experimental Example 7

Compound 72 was dissolved in a solution of polyoxyethylene hydrogenated castor oil 60/ethanol (weight ratio 20/80), and anhydrous citric acid was added as a pH adjusting agent in an amount described in Table 15 to give a drug solution. The prepared drug solution was filtrated through a 0.22 μm filter. The filtrate (1 ml) was filled in an ampoule (1P), and the head space was substituted with nitrogen and the ampoule was sealed.

A stability test was performed to give the results of Table 16. From Table 16, it was found that the pharmaceutical composition of the present invention was extremely stable.

TABLE 15

| Formulation | Formulation | Amount added |
|---|---|---|
| 7 | compound 72 | 50 mg |
|   | polyoxyethylene hydrogenated castor oil 60 | 200 mg |
|   | ethanol | 800 mg |
|   | anhydrous citric acid | 3 mg |

TABLE 16

| Formulation | Preservation condition | Dissolution sate | Residual ratio(%) | pH |
|---|---|---|---|---|
| 7 | initial | Colorless, clear | 100 | 5.0 |
|   | 60° C. × 1 week | Colorless, clear | 101.6 | 5.1 |

Experimental Example 8

40% Aqueous solution of 2-hydroxypropyl-β-cyclodextrin (hereinafter abbreviated as HP-β-CyD) (1 ml) was added to compound 72 (5 mg), and the solubility was confirmed by sonication and vortex mixing. When not dissolved, 40% HP-β-CyD solution (1 ml) was further added, and solubility was confirmed after sonication and vortex mixing in the same manner. The concentration at the time of dissolution was taken as solubility. The results are shown in Table 17.

From Table 17, the solubility of compound 72 was found to have markedly increased in the pharmaceutical composition of the present invention.

TABLE 17

| HP-β-CyD concentration | Solubility (mg/ml) |
| --- | --- |
| 40% | About 1.7 |

Experimental Example 9

An aqueous solution of maltosyl-β-cyclodextrin (hereinafter abbreviated as G2-β-CyD) at a concentration shown in Table 18 was added to compound 72 (100 mg) and the mixture was shaken at 25° C. for 3 hr. The solution was filtrated through a 0.45 μm filter, and the solubility of compound 72 was quantitatively determined by HPLC method. The results are shown in Table 18.

From Table 18, the solubility of compound 72 was found to have markedly increased in the pharmaceutical composition of the present invention.

TABLE 18

| G2-β-CyD concentration | Solubility (mg/ml) |
| --- | --- |
| 10% | 4.9 |
| 20% | 13.0 |
| 40% | 31.7 |

Experimental Example 10

A lyophilized preparation containing compound 72 and G2-β-CyD in a proportion shown in Table 19 was prepared according to the method described in the following. G2-β-CyD (145.2 mg) was added to water (1 ml) and dissolved and compound 72 (8 mg) was added and dissolved. After compound 72 was dissolved, a drug solution was filtrated using a 0.22 μm filter. The filtered drug solution (1 ml) was filled in a vial (9 P) and lyophilized under the following conditions. The solution was frozen at not higher than −50° C. for 2 hr and the temperature was raised to 0° C. at a temperature rise rate of 10° C./hr. The preparation was primarily dried for 10 hr. Thereafter, the temperature was raised to 25° C. at 10° C./hr and the preparation was secondarily dried for 6 hr. The degree of vacuum was 8.0 Pa for primary drying, and 13.3 Pa for secondary drying. For restoration of the pressure, low moisture nitrogen was used.

The content of compound 72 in the obtained preparation was 98.3% of the charged amount. When dissolved in physiological saline (1 ml), a colorless and clear solution was obtained, which remained colorless and clear at room temperature (about 23° C.) even after 24 hr from dissolution.

TABLE 19

| Formulation 8 | Amount added |
| --- | --- |
| Compound 72 | 8 mg |
| G2-β-CyD | 145.2 mg |

Experimental Example 11

The lyophilized preparation obtained in Experimental. Example 10 was subjected to a stability test to give the results of Table 20. From Table 20, it was found that the pharmaceutical composition of the present invention was extremely stable. When this lyophilized preparation was dissolved in physiological saline (1 ml), a colorless and clear solution was obtained, which remained colorless and clear at room temperature (about 23° C.) even after 24 hr from dissolution.

TABLE 20

| Preservation condition | Residual ratio |
| --- | --- |
| 50° C., 1 month | 102.4% |
| 40° C./RH 75%, 1 month | 103.5% |

INDUSTRIAL APPLICABILITY

The pharmaceutical composition of the present invention contains a water-insoluble or slightly water-soluble compound (I) having improved solubility, stability, coloring property and the like. The pharmaceutical composition of the present invention is useful as a nitrogen oxide and/or cytokine production inhibitor, for the prophylaxis or treatment of diseases such as cardiac disease, autoimmune disease, inflammatory disease, central nervous system disease, infectious disease, sepsis, septic shock and the like.

This application is based on patent application Nos. 247947/2000 and 247948/2000 filed in Japan, the contents of which are hereby incorporated by reference.

What is claimed is:

1. A pharmaceutical composition comprising (i) d-ethyl 6-[N-(2-chloro-4-fouorophenyl)sulfamoyl]-1-cyclohexene-1-carboxylate, a salt thereof or a prodrug thereof, (ii) at least one cyclodextrin derivative selected from the group consisting of maltosyl-β-cyclodextrin, glucosyl-β-cyclodextrin, hydroxypropyl-β-cyclodextrin and hydroxyethyl-β-cyclodextrin, and (iii) water.

2. The composition of claim 1, wherein the cyclodextrin derivative is maltosyl-β-cyclodextrin.

3. The composition of claim 1, which comprises about 0.1-about 100 mol of the cyclodextrin derivative per 1 mol of d-ethyl 6-[N-(2-chloro-4-fouorophenyl)sulfamoyl]-1-cyclohexene-1-carboxylate, a salt thereof or a prodrug thereof.

4. The composition of claim 1, which comprises about 1-about 5 mol of the cyclodextrin derivative per 1 mol of d-ethyl 6-[N-(2-chloro-4-flourophenyl)sulfamoyl]-1-cyclohexene-1-carboxylate, a salt thereof or a prodrug thereof.

5. The composition of claim 1, which is used as an injectable composition.

6. A pharmaceutical composition obtained by freeze-drying the compostition of claim 1.

7. A pharmaceutical composition (i) d-ethyl 6-[N-(2-chloro-4-flourophenyl)sulfamoyl]-1-cyclohexene-1-carboxylate, a salt therof or a prodrug thereof, (ii) at least on cyclodextrin derivative selected from the group consisting of hydroxypropyl-β-cyclodextrin and hydroxyethyl-β-cyclodextrin, and (iii) water.

8. A method for improving solubility in water of d-ethyl 6-[N-(2-chloro-4-flourophenyl)sulfamoyl]-1-cyclohexene-1-carboxylate, a salt thereof or a prodrug thereof, which comprises mixing said compound, a salt thereof or a prodrug thereof with at least one cyclodextrin derivative selected from the group consisting of maltosyl-β-cyclodextrin, glucosyl-β-cyclodextrin, hydroxypropyl-β-cyclodextrin and hydroxyethyl-β-cyclodextrin.

9. A method for the treatment of a cardiac disease, an autoimmune disease or septic shock, which comprises administrating an effective amount of the composition of claim 1 to a mammal.

* * * * *